US006548289B1

(12) United States Patent
Beynon et al.

(10) Patent No.: US 6,548,289 B1
(45) Date of Patent: Apr. 15, 2003

(54) BIOLOGICAL NITROGEN FIXATION

(75) Inventors: James L. Beynon, Concord, MA (US); Frank C. Cannon, Lexington, MA (US)

(73) Assignee: Land O'Lakes, Inc., Arden Hills, MN (US)

(*) Notice: Subject to any disclaimer, the term of this patent is extended or adjusted under 35 U.S.C. 154(b) by 0 days.

(21) Appl. No.: 07/826,249

(22) Filed: Jan. 27, 1992

Related U.S. Application Data

(63) Continuation of application No. 07/181,430, filed on Apr. 14, 1988, now abandoned.

(51) Int. Cl.⁷ .......................... C12P 21/06; C12P 19/34; C12N 1/20; C12N 15/00
(52) U.S. Cl. .................. 435/252.3; 435/69.1; 435/91.1; 435/252.1; 435/320.1; 536/23.1
(58) Field of Search .......................... 435/69.1, 71.1, 435/91.1, 170, 172.1, 172.3, 878, 252.1, 252.3; 536/24.1; 935/6, 9, 22, 29, 33, 38, 42, 43, 59, 60, 61, 64, 66, 72

(56) References Cited

U.S. PATENT DOCUMENTS 4,567,146 A * 1/1986 Brewin et al. ............ 435/172.3

FOREIGN PATENT DOCUMENTS

| EP | 0130047 | 1/1985 |
| EP | 0164992 | 12/1985 |
| EP | 0205071 | 12/1986 |
| EP | 0211661 | 2/1987 |

OTHER PUBLICATIONS

Craig Et Al. 1987, vol. (2) In: *Escherichia coli* and *Salmonella tyhimorium*, Cellular an Molecular Biology, P. 1054–1070, American Society for Microbiology.*
Thony, et al. (AR) 1987 Nucl. Acids Res. 15:8479.
Primrose and Ronson (AS) 1980 J. Bact. 141:1109.
Ariel Alvarez–Morales, et al.; Nucleic Acids Research; vol. 14, No. 10, 1986; pp. 4207–4227.
W.J. Buikema, et al.; Nucleic Acids Research; vol. 13, No. 12, 1985; pp. 4539–4555.

* cited by examiner

*Primary Examiner*—James Ketter
*Assistant Examiner*—Konstantina Katcheves
(74) *Attorney, Agent, or Firm*—Kinney & Lange, P.A.

(57) ABSTRACT

Method for increasing the rate of conversion of atmospheric nitrogen into ammonia in a microorganism of the genus Rhizobium, by increasing the intracellular level of an activator protein which is capable of activating the transcription of DNA of the microorganism encoding one or more proteins capable of effecting such conversion in the microorganism.

19 Claims, 20 Drawing Sheets

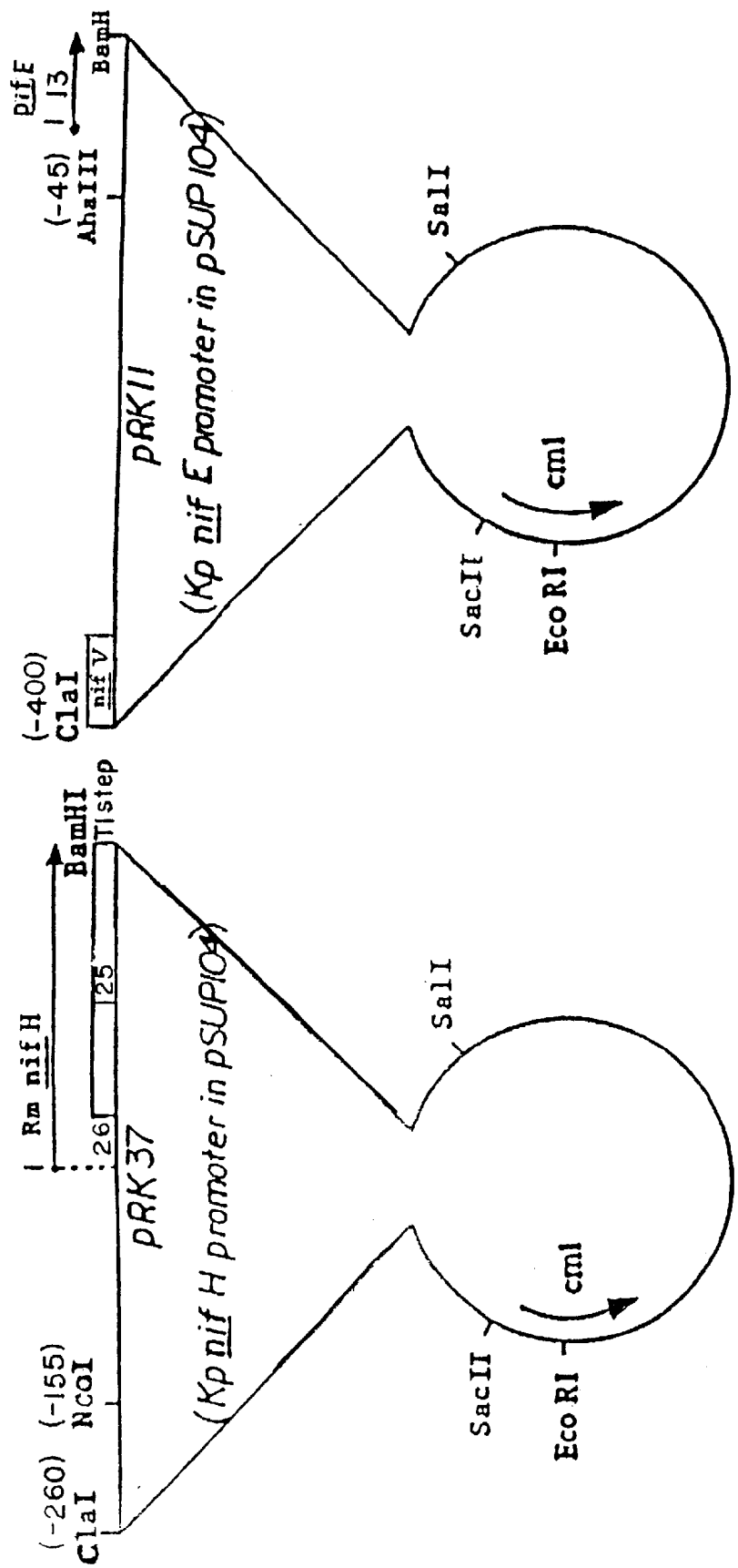

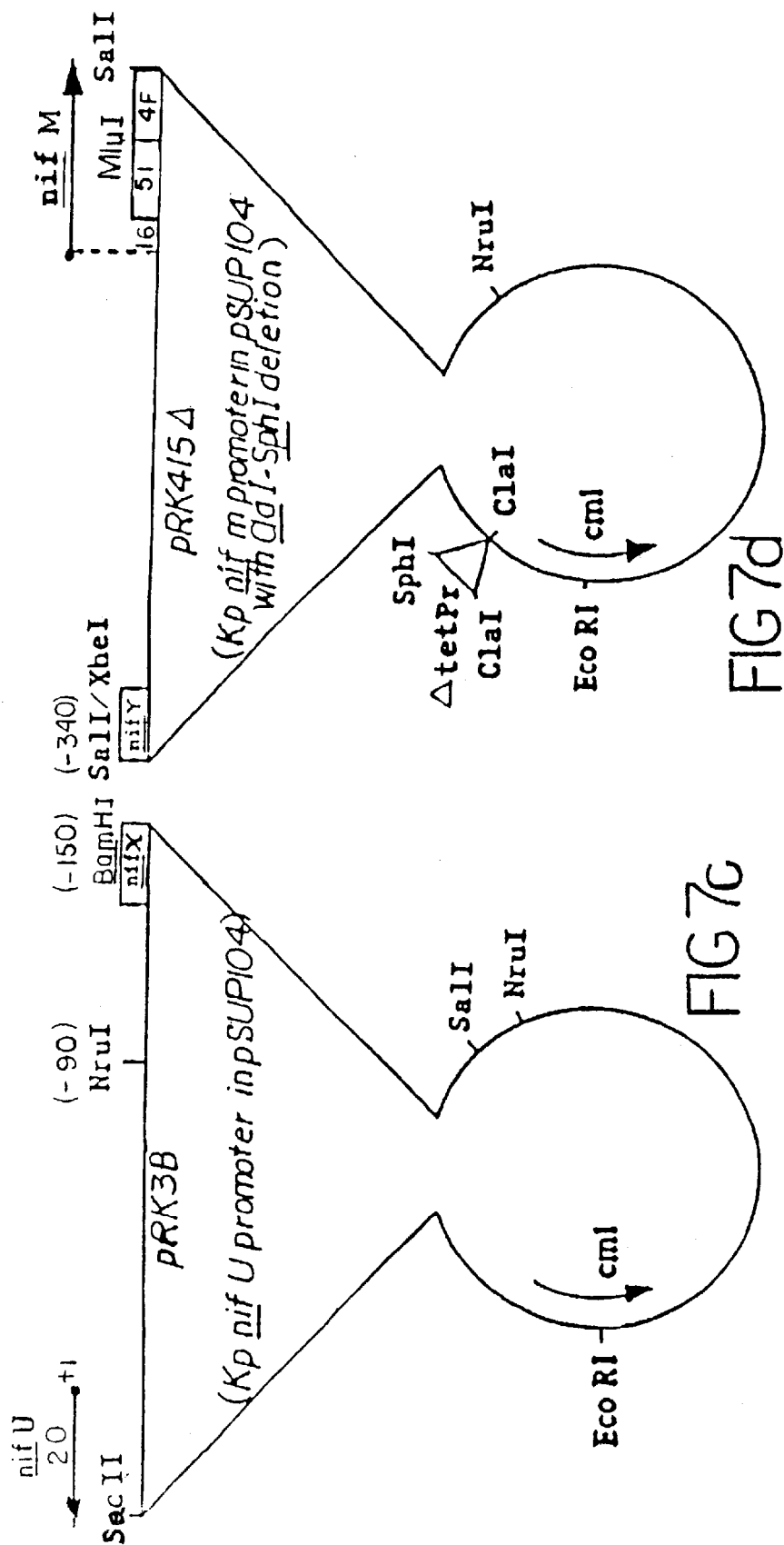

A

```
                    HgiAI
                    |
GTGCT|CCCATCGCCAACTCGTTCAGGGGAGGTAGTGCCCTGTCTGTACCT
                                                A-domain
      rbs?                  EspI
                            |
TCACAAAGAGAC |ATG|C|GC AAG CAG GAC AAC CGC TCC GCC GAA|ATT TAC AGC ATA TCA
              1                                        11 rbs?
AAG GCT CTG|ATG|GCC CCC ACT CGT CTT GAG ACC ACG CTT AAC AAT TTC GTG AAT ACC CTC
            19   EspI    SphI
                 |       |
TCT TTG ATT CTG CGC C|GC|ATG|CGC --- CAT CGC ACA|ATC AGC AGG CGT GAG CGG ACA TTT GCC
                      41                     163

C-domain                             EcoRI
                                       |
GAA GAG CAG CAA GAA CAA CAG|AAT TCA
173
```

B
```
 BglII                         rbs                SphI
 |                                                |
|GATCTGGCGAGATTTTTCAGGAGCTAAGGAAGTAAGC ATG|C
```

C
```
 SphI                                             EcoRI
 |                                                |
|CGG ACA TTT GCC GAA GAG CAG CAA GAA CAA CAG|
```

FIG.11

Insertion Vector

••••••••••• : VECTOR

∧∧∧∧∧ : HOMOLOGY REGION

———— : PROMOTER GENE FUSION

▬▬▬ : SELECTABLE MARKER

▽ : TRANSCRIPTION TERMINATOR

5'-GATCTCGGGGCCATGCTGTTGCCCATTCATGTGTCCGAACAACCGAAATAGCTTAAACAACAAGGAAGCAAGATGC-3'

Bgl IIend  BssHII

BIOLOGICAL NITROGEN FIXATION

This is a continuation of application Ser. No. 07/181,430 filed on Apr. 14, 1988, abandoned as of the date of this application.

BACKGROUND OF THE INVENTION

This invention relates to genetic engineering of agriculturally useful microorganisms.

Certain naturally occurring microorganisms, e.g., microorganisms of the genus Klebsiella, e.g., *Klebsiella pneumoniae*, and microorganisms of the genus Rhizobium, e.g., *R. meliloti* and *R. japonicum*, are capable of converting atmospheric nitrogen into ammonia ("nitrogen fixation"). It has been proposed that the slow-growing soybean-colonizing bacterial species, known for decades as *Rhizobium japonicum*, be reclassified as *Bradyrhizobium japonicum*, to distinguish it from faster growers such as *R. meliloti*, *R. phaseoli*, etc. Other newly discovered, fast-growing soybean colonizers previously classified as *Rhizobium fredii* are now known and in all the claims as *R. japonicum*. Rhizobium herein refers to all Rhizobium and Bradyrhizobium species. *R. japonicum*, as used herein with reference to the Figures and preferred embodiments, means the slow-growing bacteria now known as *B. japonicum*, and genetic constructions devised therefrom. *K. pneumoniae*, a facultative anaerobe, can fix nitrogen in a free-living state, while Rhizobium and Bradyrhizobium species normally require a symbiotic relationship with leguminous plants.

The transcendent importance of nitrogen fixation in sustaining the biosphere has been recognized for much of the present century. In the last two or three decades the world's human population has outstripped the ability of natural nitrogen fixation processes, spontaneous and biological, to support adequate food production, so that more than 30% of the world's population now depends on artificial nitrogenous fertilizer for its minimal nutrition.

In addition to Rhizobium and Klebsiella species, prokaryotes naturally able to fix nitrogen include obligate anaerobes (e.g., *Clostridium pasteurianium*), obligate aerobes (e.g., *Azotobacter vinelandii*), photosynthetic bacteria (e.g., *Rhodospirillum rubrum*), and some strains of blue-green algae (e.g., *Anabaena cylindrica*).

A symbiotic relationship can exist between Rhizobium and legumes (e.g., soybeans or alfalfa). Such a relationship begins with host-symbiont recognition and penetration of the root by Rhizobium, and culminates in the differentiation of the bacterium into the nitrogen-fixing "bacteroid" form within the root nodule. It is only in the bacteroid form that nitrogen is fixed by Rhizobium. Rhizobium species exhibit host-range specificity: for example, *R. japonicum* infects soybeans, and *R. meliloti* infects alfalfa.

The plant species commonly used in commercial agriculture cannot fix their own nitrogen unless in symbiotic association with nitrogen fixing microorganisms and are thus reliant, in general, on the addition of nitrogenous fertilizers. However, the symbiotic relationships between legumes and Rhizobium have long been exploited in commercial agriculture. Various strains of Rhizobium are currently sold commercially, to be used as "inoculants" to increase the yields of legume crops such as soybean, alfalfa, and closer. Rhizobial inoculants have been sold in significant volume in the U.S. since 1959, and it has been estimated by the USDA that 50% of the total U.S. acreage of soybean crops and 80% of alfalfa crops are inoculated.

Although rhizobial products are used to such an extent in this country, the existing products are believed not to be very effective in promoting yield increases. One reason for this might be poor competition between the introduced strains and those strains indigenous to the soil.

In nitrogen fixing microorganisms there are genes coding for products involved in the nitrogen fixation pathway. In *K. pneumoniae*, these genes are known as the "nif" genes. Analogous sets of genes are present in other nitrogen fixing species (perhaps arranged differently in each species). The nif genes of *K. pneumoniae* are arranged in sequence in 7–8 operons. One operon contains the structural genes coding for the protein subunits of the major enzyme in the nitrogen fixation pathway, nitrogenase. The nitrogenase operon is composed of a promoter (the nifH promoter); the three subunit structural genes, nifH, nifD, and nifK; and the nifT and nifY genes, of unknown function. Another operon is composed of a promoter and the nifL and nifA genes. The nifA gene encodes a transcriptional activator protein, the nifA protein, which is required for the expression of all operons containing the nif genes, except its own. The nifL gene codes for a protein which renders the nifA transcriptional activator protein nonfunctional, and thus serves to repress nitrogen fixation. (References herein to the nifA gene, the nifL promoter, and the nifH gene and promoter are intended to include DNA derived from *K. pneumoniae*, as well as functionally equivalent DNA derived from any other nitrogen fixing bacteria.)

Buchanan-Wollaston et al., 1981, Nature 294:776 report an investigation of the role of the nifA gene product in the regulation of nif expression. A variety of *Klebsiella pneumoniae* strains were transformed with either of two plasmids constructed to permit constitutive expression of the nifA gene product. In pMC71A the nifA gene was cloned into the tetracycline resistance gene of the plasmid pACYC184 and transcribed from the promoter of the tetracycline resistance gene. In pMC73A, the nifA gene was cloned into the kanamycin resistance gene of the plasmid pACYC177 and transcribed from the promoter of the kanamycin resistance gene. Expression of nifA from these plasmids was tested in a mutant-strain of *K. pneumoniae* which does not express normal nifA activity. Both plasmids were observed to complement the nifA mutation. Constitutive nif expression in the presence of $NH_4^+$ (a negative effector of nif transcription initiation) was also examined by measuring β-galactosidase activity in a *K. pneumoniae* strain using a genomic fusion of the nifH promoter in reading frame with the lacZ gene.

SUMMARY OF THE INVENTION

The present invention provides a strategy for improving crop yields, involving increasing nitrogen fixation in nitrogen fixing bacteria via genetic engineering.

In general, the invention features a vector for transforming a host microorganism which contains DNA encoding one or more proteins capable of effecting the conversion of atmospheric nitrogen into ammonia in the microorganism, the vector being capable of increasing the capacity of the microorganism to so convert atmospheric nitrogen, the vector including a gene encoding an activator protein capable of activating the transcription of that DNA, the activator protein-encoding gene preferably being under the transcriptional control of an activatable promoter sequence.

Microorganisms transformed with the vector have an improved capacity to fix nitrogen. The activator protein which is normally present in only a limited amount is, by virtue of the vector, produced in a much greater amount which results in increased production of nitrogenase from the nif genes of the host microorganism (although too great an amount of the activator protein can actually be detrimental to plant growth). Thus, even in the presence of a nifL-like repressor protein, there is sufficient overproduction of nifA protein to activate nitrogenase production. Furthermore, the use of an activatable promoter allows for high levels of nifA protein production at the time the host cell initiates nitrogen fixation.

Alternatively, the same effect can be achieved by placing the inserted nifA gene under the transcriptional control of a constitutive promoter, e.g., the promoter of a bacterial gene for kanamycin resistance.

Nitrogen fixing bacteria transformed with a vector of the invention, living in association with legume crops with which the bacteria can live symbiotically, can increase the yields of those crops by virtue of the improved nitrogen fixation provided by the bacteria.

The invention also features a method for stably integrating, by homologous recombination, a DNA sequence into a silent region of the Rhizobium chromosome. This method can be used for integrating a cloned gene of the invention, capable of increasing the microorganism's ability to convert atmospheric nitrogen, or any other desired gene.

Other features and advantages of the invention will be apparent from the following description of preferred embodiments thereof, and from the claims.

DESCRIPTION OF THE PREFERRED EMBODIMENTS

We now describe preferred embodiments of the invention, after briefly describing the drawings.

Drawings

FIGS. 7a–7d are diagrammatic representations of vectors containing the K. pneumoniae nifH(a), K. pneumoniae nifE (b), K. pneumoniae nifU(c), and K. pneumoniae nifM(d) promoters.

FIG. 11 is the nucleotide sequence of the 5' end of the R. meliloti nifA gene (A) and oligonucleotides (B, C) used in the construction of derivatives thereof.

Vector Components

Figure 1:
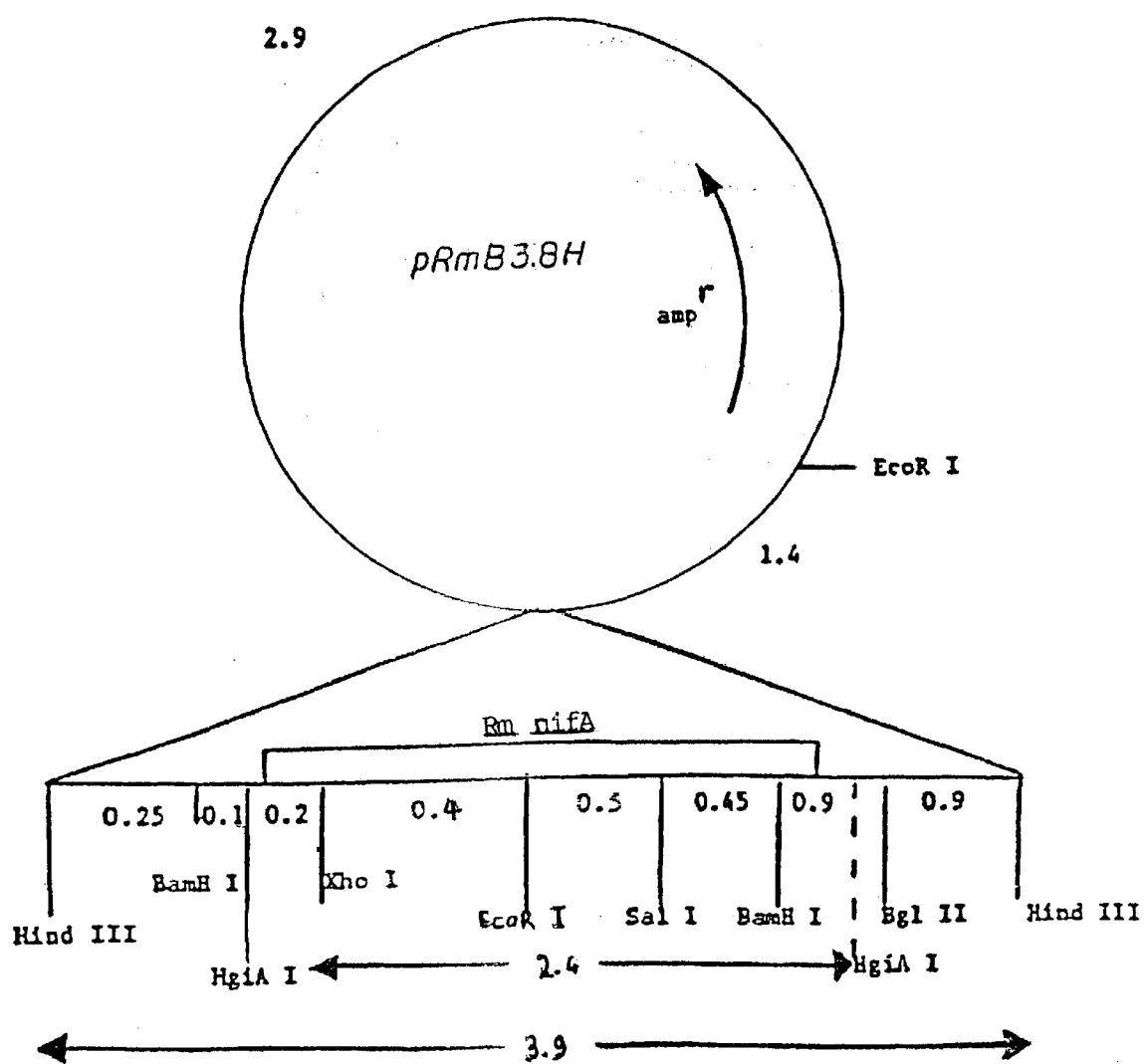
FIG. 1 is a diagrammatic representation of the vector pRmB3.8H, containing the R. meliloti nifA gene.

As mentioned above, the vectors of the invention contain several essential DNA regions and sites, now described in greater detail.

Transcriptional Activator Gene and Promoter Sequence

According to the invention, a plant's ability to assimilate nitrogen by virtue of its symbiotic association with a nitrogen fixing bacterium is increased by the introduction of a bacterium, preferably Rhizobium, which has been transformed with a vector which contains a gene for an activator protein, under the transcriptional control of a promoter, preferably an activatable promoter. Any suitable activator protein can be used, in conjunction with any suitable promoter. The most preferred activator protein gene/promoter combination is a nifA gene, under the transcriptional control of a nif promoter, e.g., a nifH promoter. The following is a more detailed description of the nif system and the operation,of these two components in nature and according to the invention.

As is mentioned above, the product of the nifA gene is a transcriptional activator protein required for the initiation of transcription of the promoters of all the nif operons except its own. The gene product of nifL acts as a repressor of nif transcription by combining with the nifA protein and inactivating it, preventing the activation of nif transcription and expression of the nitrogen fixation pathway. The nifL repressor is, in its active form, able to sequester the nifA protein only under intracellular conditions of high fixed nitrogen or oxygen concentration. Under conditions of low intracellular fixed nitrogen concentration, the nifL repressor is inactive. The nifA and nifL protein thus make up a feedback inhibition loop which shuts down nitrogen fixation when fixed nitrogen and oxygen are present at high concentrations.

Another nif operon is composed of nifH, nifD, nifK, nifY and nifT. The first three genes of the operon code for subunits of the chief enzyme of the nitrogen fixation pathway, nitrogenase. Of all the nif operon promoters, the nifH promoter probably has the highest affinity for the nifA activator protein; the nifH promoter binds the activator so tightly that, if multiple copies of the nifH promoter (carried on plasmids) are introduced into a cell, they will titrate out all of the nifA protein present. This high affinity is believed to be the reason the nifH promoter is the strongest of the nif promoters.

The nifA gene, engineered to be transcribed under the control of the nifH promoter, effects an increased intracellular concentration of nifA protein. This increased concentration cannot occur naturally because the feedback inhibition system causes derepression of the nif system and increased nitrogenase production with concomitant nitrogen fixation independent of intracellular fixed nitrogen or oxygen concentrations.

Although the nifA gene is substantially homologous between species, the sequences are not identical. Thus, it is preferable according to the invention to employ a nifA gene or portion thereof identical to that of the host microorganism (e.g., the R. meliloti gene in an R. meliloti host). There can be employed either the intact nifA gene or a derivative in which the corresponding N-terminal domain, which may be involved in binding the nifL repressor, is deleted. Deletion of this domain renders the nifA protein a more efficient promoter activator. Drummond et al. (1986, EMBO J. 5:441) aligned the amino acid sequences of the nifA proteins of R. meliloti and K. pneumoniae and showed that there are domains of homology separated by less similar segments of variable lengths. The N-terminal homologous domains of the nifA proteins (collectively referred to as domain A which extends from amino acid 10 to amino acid 163 of R. melitoti nifA, and from amino acid 22 to amino acid 182 of K. pneumoniae nifA, Drummond et al., supra.) were determined to be functionally involved with the repression of nifA promoter activation. We found that the deletion of a region encompassing amino acids 2 through 166, which includes domain A, rendered the nifA protein a more efficient transcriptional activator, probably due to the lack of the repressor binding region.

In addition to regulated (i.e., activatable) promoters such as the nif promoters, a promoter which can constitutively effect transcription of the nifA gene, e.g., the readily available promoter from the kanamycin resistance gene can also be used.

Selectable Marker

Because transformation of microorganisms with plasmids is a relatively rare event, plasmids of the invention preferably contain a DNA region which encodes a selectable marker protein for the identification of transformants. This marker protein can be any protein which can be expressed in host cells and which enables the phenotypic identification of microorganisms which express the protein. Preferred marker proteins are proteins which confer resistance to one or more antibiotics, e.g., chloramphenicol. Transformants are those microorganisms able to grow in the presence of the antibiotic.

Plasmid Construction

Plasmids can be constructed using a number of different combinations of promoters and nifA genes. The R. meliloti nifA gene, in combination with any of several promoters, is used for transformation of R. meliloti; the B. japonicum nifA gene, in combination with suitable promoters, is used with B. japonicum.

NifA Genes

R. meliloti nifA Gene

The R. meliloti nifA gene is obtained from a 2.4 kb HgiAI fragment of plasmid pRmB3.8H (FIG. 1, and described in Szeto et al., 1984, Cell 36: 1035). The sequence of the R. meliloti nifA gene is given in Buikema et al., 1985, Nuc. Acid Res. 13: 4539.

B. japonicum nifA Gene

Figure 2:
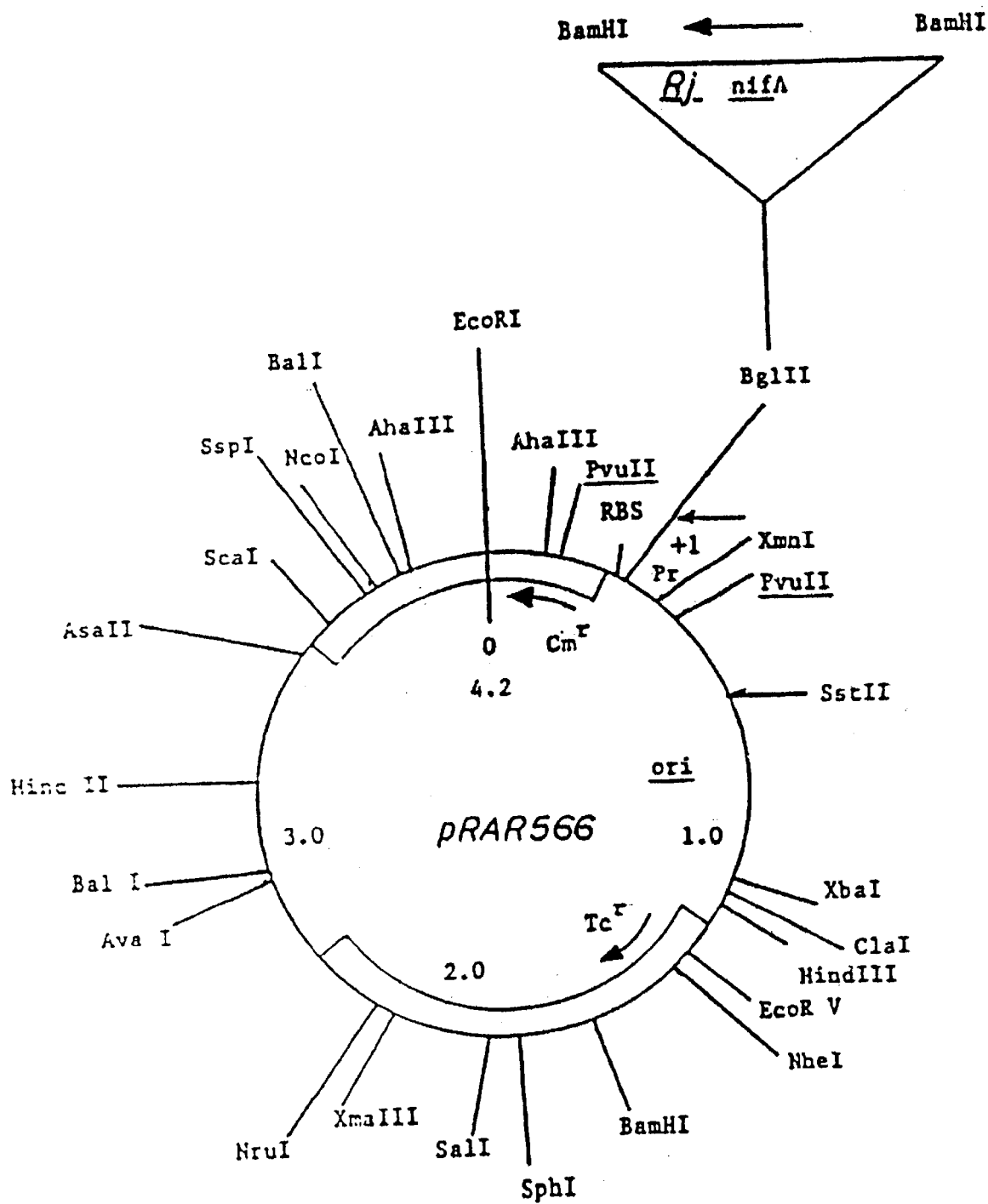
FIG. 2 is a diagrammatic representation of the vector pRAR566, containing the R. japonicum nifA gene.

The nifA gene of B. japonicum 110 is located immediately upstream of the putative fixA gene. Using a 20-mer oligonucleotide based on the B. japonicum fixA coding sequence (5' CCGGACTCGGCGCAGATCCG3') as a probe, we determined that both genes are located on a 5.4 kb HindIII-BamHI fragment of the B. japonicum genome. To isolate this fragment, B. japonicum DNA was digested with BamHI and separated on a sucrose gradient. Fractions containing large (20–25 kb) fragments showed the highest levels of hybridization to labelled 20-mer probe. This DNA was digested with HindIII and ligated into pBR327 that had been treated with HindIII, BamHI, and alkaline phosphatase. The 5.4 kb fragment, which includes both the nifA and fixA genes, was recovered from an E. coli transformant on a plasmid called pFCC301. A 3.46 kb HincII-PstI fragment spanning the nifA gene was removed from pFCC301 and cloned into the BglII site of pJB120 (derived from pACYC184 by changing the TagI site between the Shine-Dalgarno (SD) sequence and transcription start site to BglII, FIG. 6) after conversion of the termini to BamHI sites using oligonucleotide linkers. This subcloning was done to separate the fixA gene from the nifA fragment. The resulting plasmid, pRAR566, is the storage vector for the B. japonicum nifA gene (FIG. 2). The nucleotide sequence of the nifA gene was determined and is given in Thony et al, 1987, Nucl. Acid Res. 15:8479.

R. meliloti nifA gene with domain A deleted

Plasmid pJB203, with domain A of the nifA gene deleted, and the naturally occurring Shine-Dalgarno sequence replaced with a superior synthetic SD sequence was constructed as described below. pJB182, which contains a modified form of the nifA gene fused to the E. coli cat promoter was used as the starting plasmid. Plasmid pJB182 was derived by replacing the natural SD sequence of the nifA gene in plasmid pJB160 with a synthetic SD sequence that has a stronger binding affinity for ribosomes and then replacing the fixA promoter of pJB160 with the cat promoter. The natural sequence of the 5' end of the nifA gene, and 61 base pairs extending upstream, are shown in FIG. 11, Panel A. A synthetic DNA fragment which encodes a more efficient SD sequence (shown in Panel B) was cloned into the DNA sequence of Panel A, following digestion of pJB160 with BglII and FspI (partial) to remove the natural SD sequence, creating pJB180. An SphI site was introduced into pJB180 at the 3' end of the linker fragment. The fixA promoter of pJB180 was then replaced by the cat promoter, creating pJB182.

The deletion of domain A from pJB182 was achieved by the following procedure. The sequence extending from amino acid position 2 through amino acid position 168 of the nifA protein was deleted by cleaving pJB182 with SphI and EcoRI and replacing the deleted fragment with the oligonucleotide shown in Panel C of FIG. 11. This resulted in the deletion of all of domain A and re-created the last four amino acids of the linker region between domains A and C (amino acids 169–172) and the first seven amino acids of domain C preceding the EcoRI site (amino acids 173–179). The resulting plasmid is pJB203.

Promoters

Various promoters have been isolated for ligation to the above or other nifA genes, and in order to express the nifA gene at suitable levels to cause increased nitrogen fixation. Certain guidelines can be followed to determine if a promoter is likely to produce optimal nifA expression. These guidelines are not meant to exclude any potentially useful promoters and it is recognized that exceptions to these guidelines will be found. Nevertheless, the guidelines can be generally applied to the process of choosing appropriate promoters for increased production of nifA leading to an increased nitrogen fixing capacity.

In general, strong constitutive promoters should be avoided. We have discovered that the production of nifA above an optimal level is detrimental to plant growth. Strong unregulated expression of the nifA gene results in the production of levels of nifA protein that inhibit the growth of the plant. Similarly, strong homologous promoters (i.e., promoters found naturally in the same bacterium) should be avoided. A strong homologous promoter will also lead to the production of excessive amounts of nifA, which are detrimental to the plant. Thus, we have found that strong heterologous promoters (i.e., promoters not naturally occurring in the bacterium) are the most suitable for providing increased nifA production, at a level that is beneficial, not deleterious, to the plant. Nif promoters are generally less active in a nonhomologous environment, and therefore, a strong nif promoter in a heterologous host will express adequate, elevated, levels of nifA protein. Examples of such promoters follow.

B. japonicum nifH Gene Promoter

Figure 3:
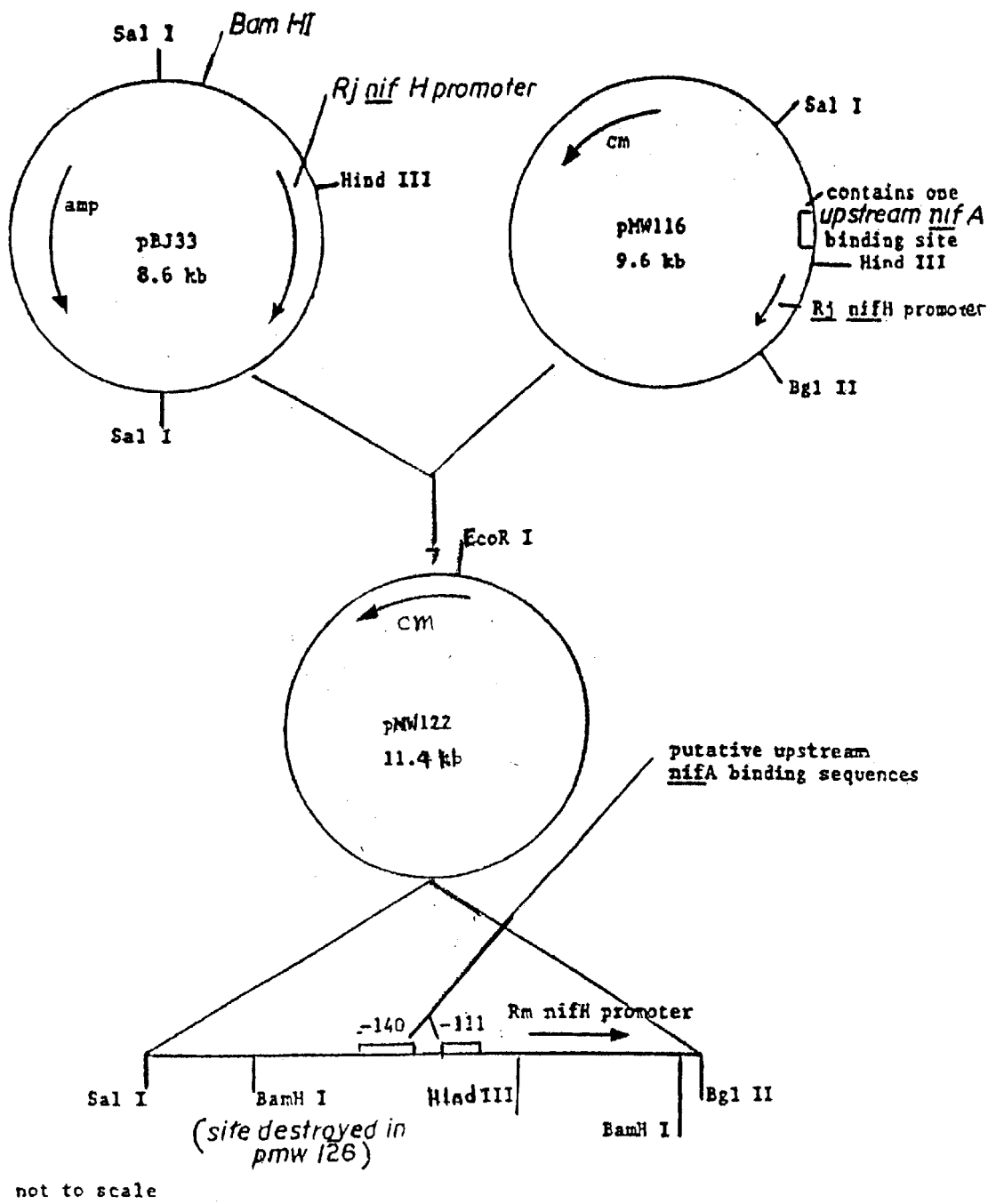
FIGS. 3 and 5 are diagrammatic representations of the vectors pMW122 and pJB81, containing the R. meliloti nifH promoter.

The nucleotide sequence of the B. japonicum nifH promoter is described in Fuhrmann and Hennecke, 1984, J. Bact. 158:1005. Referring to FIG. 3, the B. japonicum nifH promoter is carried on pBJ33 (obtained from Barry Chelm at Michigan State University), on a SalI insert in pBR322.

A region containing the B. japonicum nifH promoter was isolated on a 0.15 kb BglII-HgiAI fragment. The HgiAI end was converted to a BamHI site using a linker, and this fragment was cloned into the BamHI site of pBR322 to give pMW115. The BamHI-SalI fragment of pMW115, with the BamHI site converted to BglII by a linker, was cloned into the ClaI-SalI site of pSUP104, a broad host-range vector described by Simon et al. in Molecular Genetics of the Bacteria Plant Interaction 98–106, A. Puhler ed. 1983; and Puhler et al. U.S. Pat. No. 4,680,264, hereby incorporated by reference. The ClaI site was converted to BglII using a linker, to give pMW116 (FIG. 3).

The B. japonicum nifH (and nifA, see below) promoter contains conserved putative upstream nifA binding sequences, described in Buck et al., 1986, Nature 320: 374. Deletion or mutation of these conserved sequences has been shown to result in a decrease in promoter strength in E. coli (Alvarez-Morales et al., 1986, Nucl. Acid Res. 14: 4207). The B. japonicum nifH promoter contains two upstream nifA binding sites, one located at –111 and the other at –140 relative to the +1. On analysis, pMW116 was found to contain only the binding site at position –111. The other site, located at –140, was inadvertently deleted.

In order to clone the nifH promoter including the –140 site, the vector pMW116 was modified in order to include both upstream nifA binding sequences, as follows. A 1.85 kb HindIII-SalI fragment from pBJ33 containing both putative upstream binding sequences was cloned into the HindIII-SalI site of pMW116, replacing a fragment which contained only one binding sequence (FIG. 3). The resulting plasmid, pMW122, was partially BamHI digested, filled in and religated, in order to eliminate the BamHI site upstream from the nifA binding sequences. The resulting plasmid, pMW126, allowed for cloning into the BamHI linker site downstream from the B. japonicum nifH promoter, and serves as a storage vector for the B. japonicum nifH promoter.

Activation of nifH Promoted Gene Expression

Figure 13:
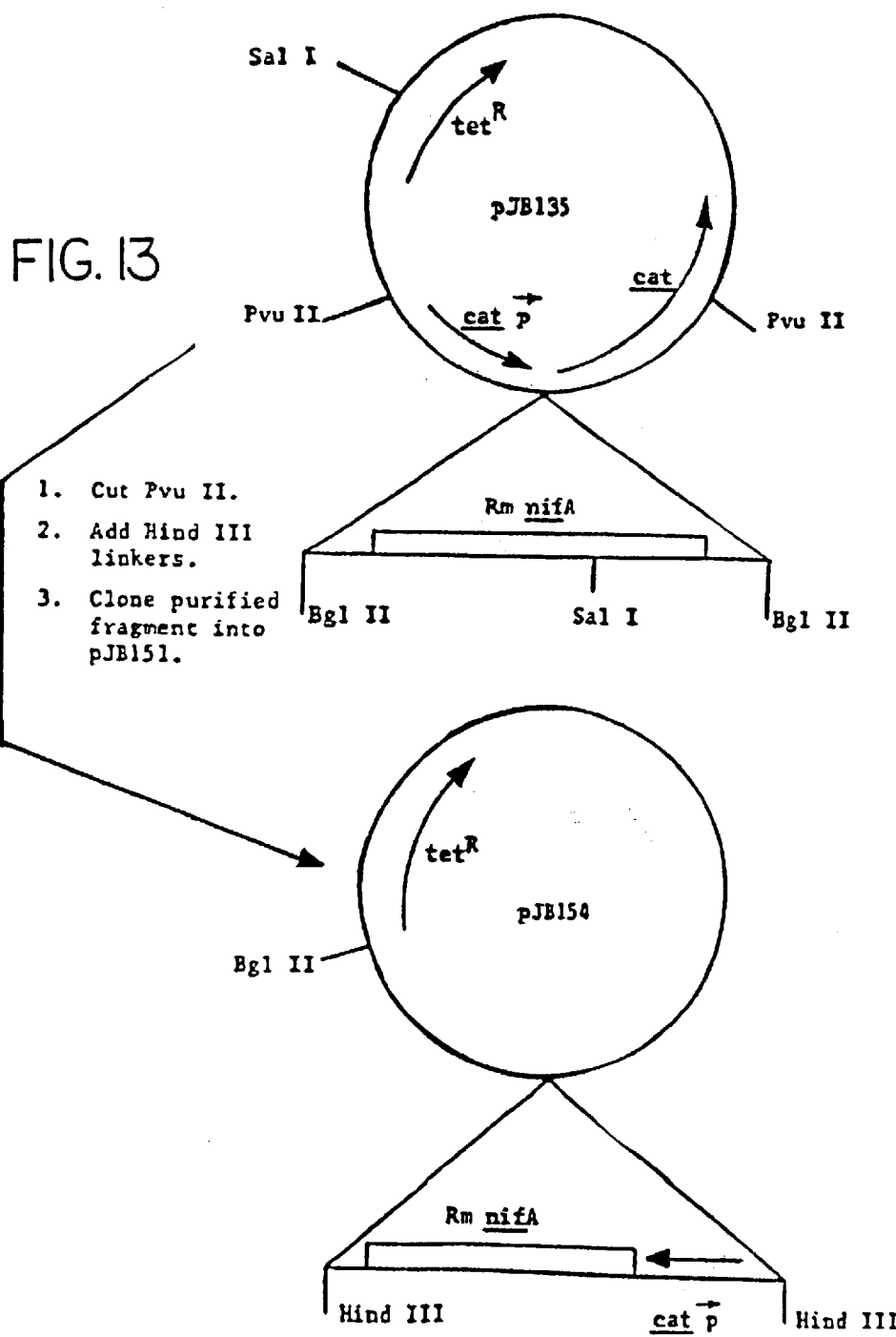
FIG. 13 is a diagrammatic representation of the construction of the vector pJB154, containing the cat promoter fused to the R. meliloti nifA gene.

Data presented in Table 1 show a comparison of the level of gene expression from the nifH promoter of either K. pneumoniae or R. meliloti when activated with one of three versions of the nifA gene product. In the test plasmids, all forms of the nifA gene are expressed from the E. coli cat promoter. Referring to FIG. 13, pJB135 containing the nifA gene with its natural SD sequence was constructed by cloning the BqlII fragment from pJB131 (derived from pJB110, infra, by changing one NruI site 24 bp past the end of the nifA gene to a BglII site), containing the nifA gene, into BglII digested pJB120. The nifA protein expressed from pJB135 causes expression of lacZ from the nifH promoter at a level only slightly higher than background. In pJB182, in which the nifA gene is fused to the synthetic SD sequence, expression of the lacZ gene from the R. meliloti promoter is increased approximately 2.4-fold above background. The increase in β-galactosidase expression is much more pronounced when the synthetic SD sequence is fused to the nifA gene which has been deleted for domain A (pJB203). In this case, expression from the nifH promoter is enhanced 15-fold above background.

TABLE I

Activation of promoters by nifA protein

|  | K.p. nifH P::lacZ (pJB31) | R.m. nifH P::lacZ (pVSP9) |
| --- | --- | --- |
| pJB120 | 2.1 | 850 |
| pJB135 | 3.3 | 909 |
| pJB182 | 16.4 | 2028 |
| pJB203 | 1853.0 | 12649 |

B. japonicum nifD Gene Promoter

Figure 4:
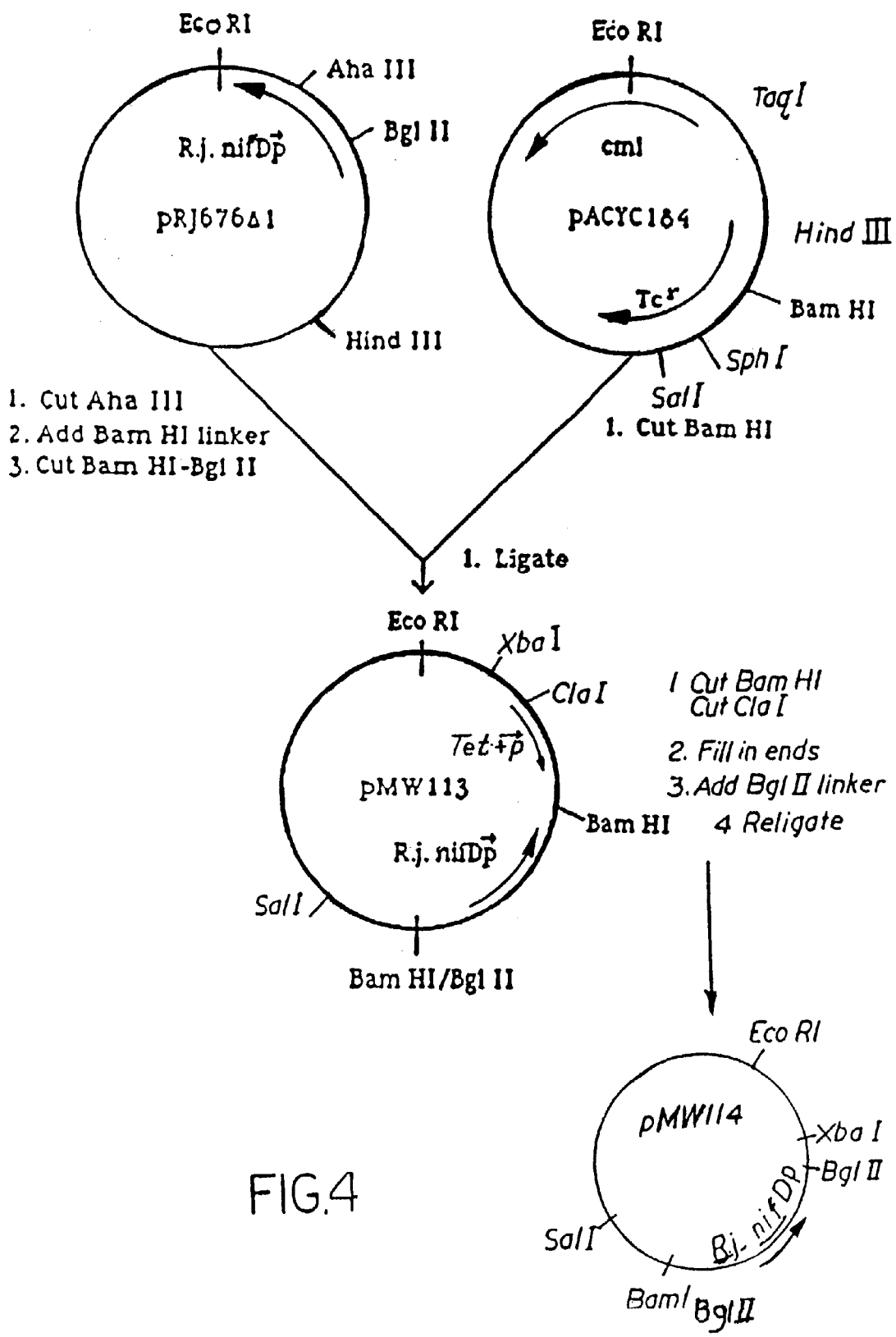
FIG. 4 is a diagrammatic representation of the construction of the vector pMW113, containing the R. japonicum nifD promoter.

The nucleotide sequence of the B. japonicum nifD promoter is described in Kaluza and Hennecke, 1984, Mol. Gen. Genet. 196:35. Referring to FIG. 4, the B. japonicum nifD promoter is carried on pRJ676Δ1 (obtained from Barry Chelm), a derivative of pRJ676 (Hennecke, 1981, Nature 291:354). The B. japonicum nifD promoter was isolated from pRJ676Δ1 on the 370 bp AhaIII to BglII fragment. The AhaIII end was converted to BamHI using a linker. The BamHI-BglII fragment was then subcloned into the BamHI site of pACYC184 to give pMW113. The tetracycline resistance promoter was deleted by cutting with ClaI and BamHI and inserting a BglII linker to give pMW114. This gave a tailored version of the B. japonicum nifD promoter, allowing genes to be expressed from the nifD promotor by inserting them into the BglII site of pMW114. The XbaI-SalI fragment of pMW114 was cloned into XbaI+SalI cut pSUP104, to give pMW117.

Chloramphenicol acetyl transferase (cat) promoter

The nucleotide sequence of the E. coli cat promoter is given in Alton et al., 1979, Nature 282:864. The promoter for the cat gene is a constitutive promoter carried on pJB120, which was constructed by converting a TaqI site of pACYC184 (FIG. 4) to a BglII site using an oligonucleotide linker. This site lies between the transcriptional start and the SD sequence of the cat gene and provides a convenient location for cloning genes under cat promoter control.

R. meliloti nifH Gene Promoter

Figure 5:
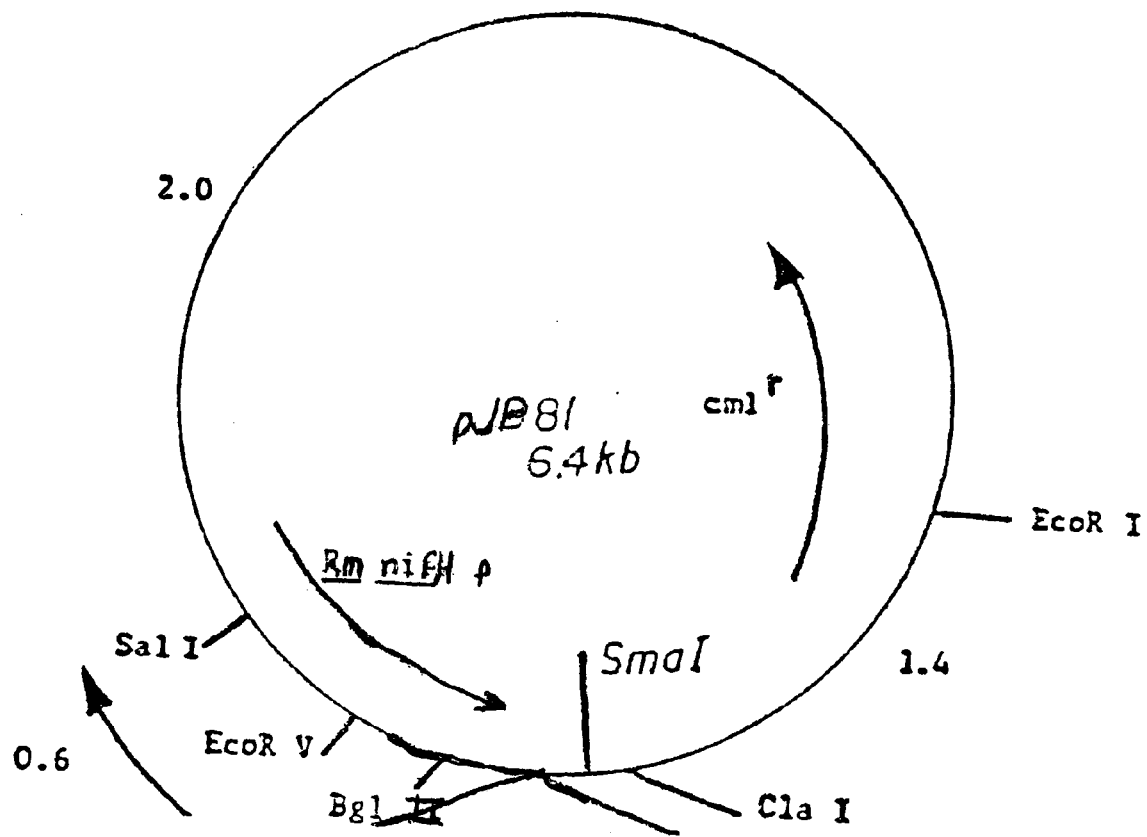

The nucleotide sequence of the R. meliloti nifH gene promoter is given in Sundaresan et al., 1983, Nature 301:728. Referring to FIG. 5, there is shown plasmid pJB81, containing the R. meliloti nifH promoter. pJB81 was constructed by first cloning a 680 bp SalI-SphI fragment from pRmR2 (Ruvkun et al., Nature, 1981, 289:85) into SalI-SphI digested pACYC184, then digesting the resulting plasmid (pJB80) with SphI and HindIII and ligating in SmaI linkers. This created a unique SmaI site immediately downstream of the R. meliloti nifH promoter sequence.

R. meliloti fixA Gene Promoter

Figure 6:
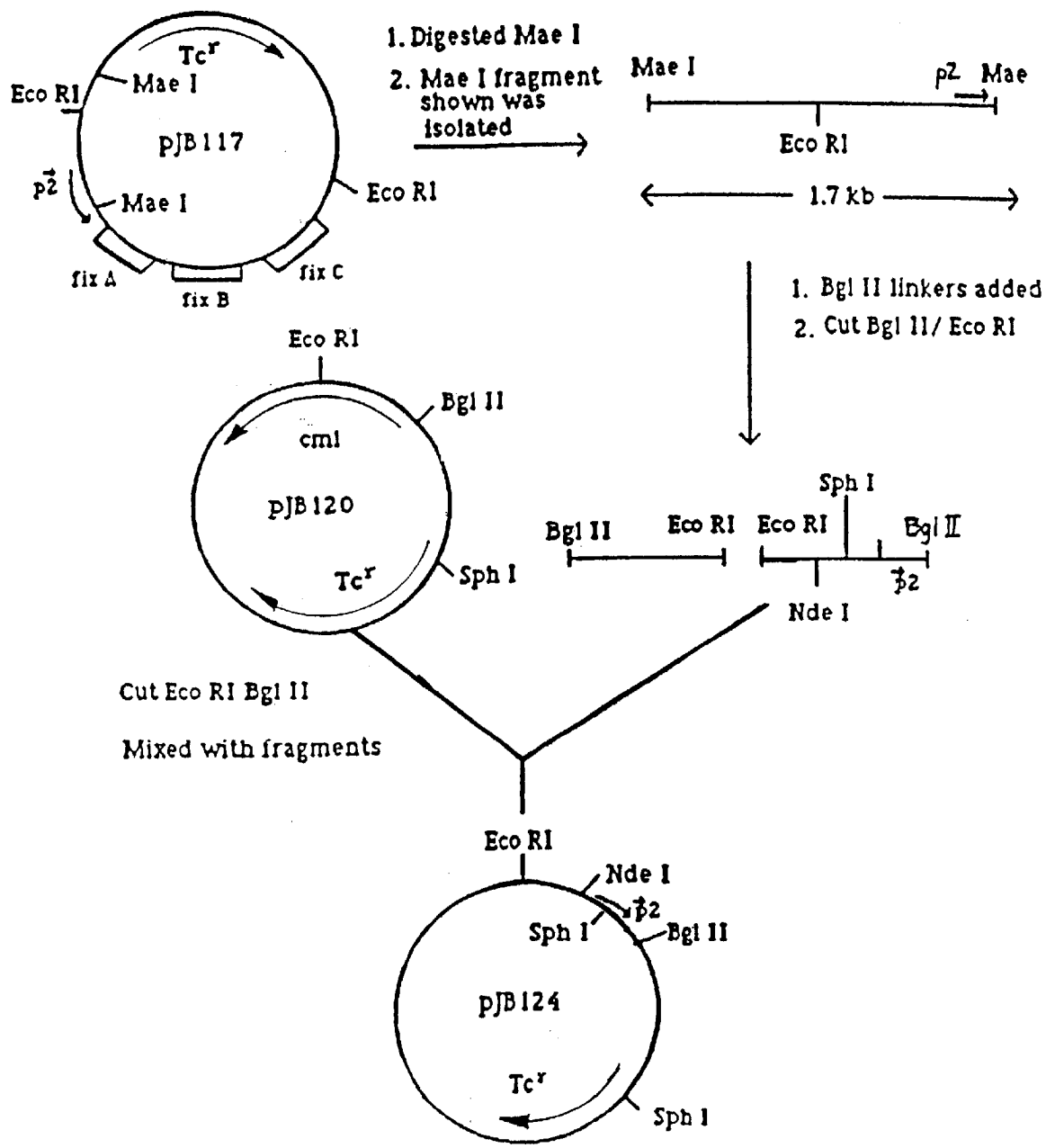
FIG. 6 is a diagrammatic representation of the construction of vector pJB124, containing the R. meliloti fixA promoter.

The nucleotide sequence of the R. meliloti fixA gene promoter is given in Earl et al., 1987, J. Bact. 169:1127. The R. meliloti fix gene cluster was isolated on a 5 kb EcoRI fragment from plasmid pWB1083 (obtained from F. Ausubel, Buikema et al., 1983, J.Mol. Appl. Genet., 2:249). This EcoRI fragment was cloned into the EcoRI site of pACYC184 (FIG. 4) to give pJB117 (FIG. 6). A MaeI site was identified at the +2 position relative to the transcription start site. The fixA promoter region was removed from pJB117 by cleavage with MaeI, conversion of the MaeI ends to BglII ends with synthetic linkers, and then EcoRI and BglII digestion. The fragment containing the fixA promoter region was ligated into EcoRI+BglII digested pJB120 to create pJB124 (FIG. 6).

K. pneumoniae nifH Gene Promoter.

The nucleotide sequence of the K. pneumoniae nifH gene promoter is given in Sundaresan et al., (1983, Nature 301:728) and Scott et al., (1981, J. Mol. Appl. Genet. 1:71). The K. pneumoniae nifH promoter was isolated from pKA3 (pACYC184 having a 0.6 kb EcoRI-BglII fragment of pVW16, described by Buchanan-Wollaston et al., 1981, Mol. Gen. Genet. 184:102, inserted at the EcoRI site) on a 471 bp EcoRI-SacII fragment and cloned into ClaI and BamHI digested pSUP104, resulting in pRK37 (FIG. 7a).

The fragment containing the nifH promoter also contained part of the nifJ promoter region which is transcribed in the opposite direction from a site further upstream. The nifH promoter was thus cloned independent of the nifJ promoter region by removing the NcoI-BamHI fragment from pRK37 and recloning it into NcoI-BamHI digested pJB120. The resulting plasmid is designated pRK372.

K. pneumoniae nifE Gene Promoter.

The nucleotide sequence of the K. pneumoniae nifE gene promoter is described in Beynon et al., 1983, Cell 34:665. The K. pneumoniae nifE promoter was isolated on a SmaI-HincII restriction fragment from pVW10 (pBR322 containing the EcoRI-SalI nifE promoter fragment of K. pneumoniae inserted at the EcoRI-SalI sites; Beynon et al. Cell 34:665). The SmaI-HincII ends were converted into ClaI and BamHI ends and inserted into ClaI+BamHI digested pSUP104, creating pRK11. (FIG. 7b).

K. pneumoniae nifU Gene Promoter.

The nucleotide sequence of the K. pneumoniae nifU gene promoter is described in Beynon et al., (id.). The K. pneumoniae nifU promoter was isolated from pMC11 (pBR322 containing the nifU fragment from K. pneumoniae) on a BamHI-SacII fragment and cloned directly into the BamHI-SacII sites of pSUP104, to create pRK3B (FIG. 7c).

K. pneumoniae nifM Gene Promoter.

The nucleotide sequence of the K. pneumoniae nifM gene promoter is given in Beynon et al., (id.). The K. pneumoniae nifM promoter was subcloned on a XhoI-SalI fragment from pMC12 (pBR322 containing the EcoRI-PstI nifM promoter fragment of K. pneumoniae, Beynon et al. Cell, supra.) into the SalI site of pSUP104, resulting in pRK415. The promoter for the tetracycline resistance gene was subsequently removed by deleting plasmid sequences between the ClaI site and the SphI site. The resulting plasmid is designated pRK415Δ (FIG. 7d).

Construction of Broad Host Range Vector pJB151

Figure 8:
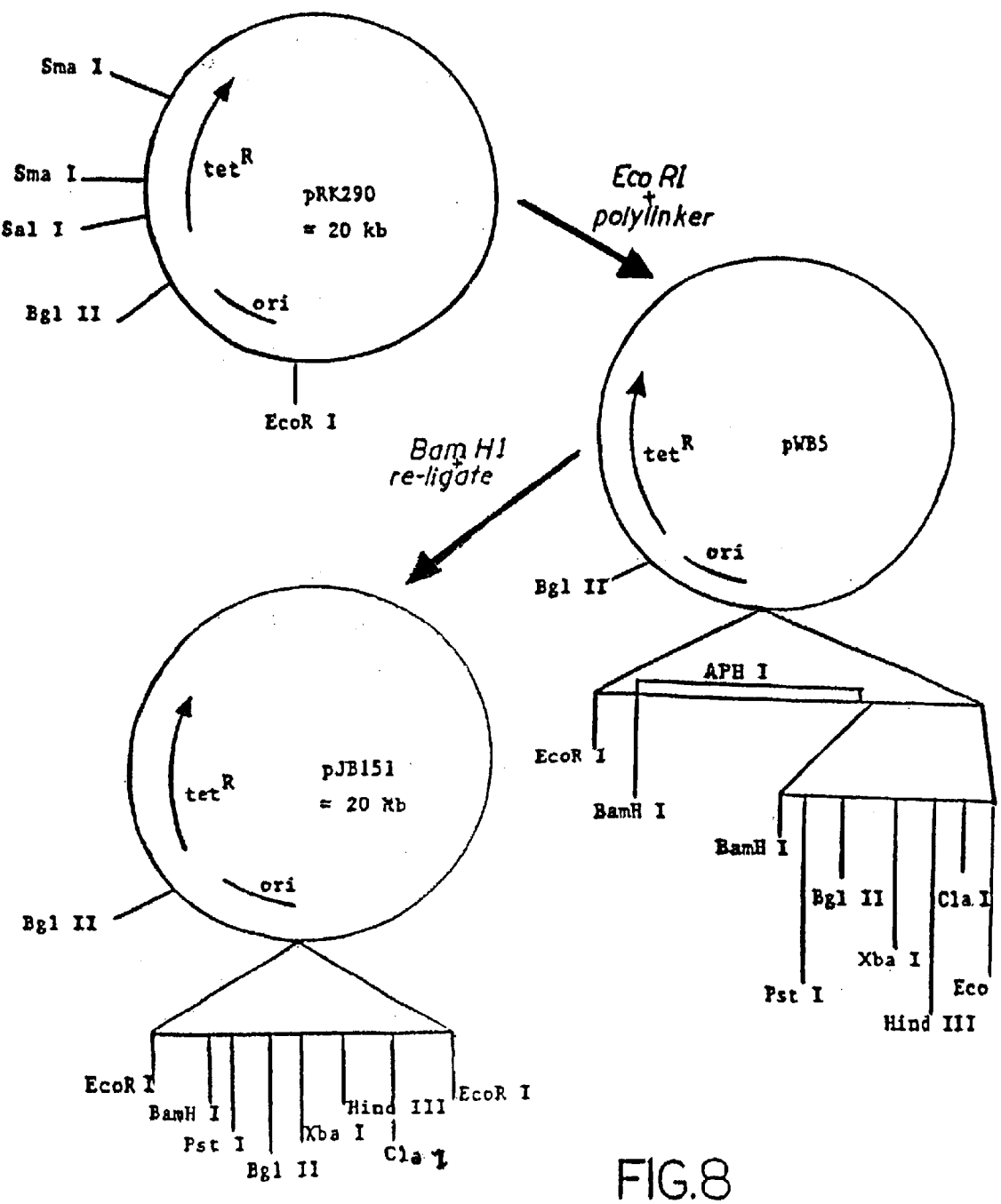
FIG. 8 is a diagrammatic representation of the construction of the broad host-range vector pJB151.

Fusions of nifA genes to suitable promoters are transformed into Rhizobium using broad host range vectors, for example, pSUP104. We found that pSUP104 may have an inherent detrimental effect on nitrogen fixation when transformed into R. meliloti. Referring to FIG. 8, we therefore chose to use a derivative of a different broad host range vector, pRK290 (Helinski U.S. Pat. No. 4,590,163, hereby incorporated by reference), which we showed had no such detrimental effect. The derivative vector, pJB151, was constructed as follows.

We began with plasmid pWB5, made by inserting the kanamycin resistance gene and a multiple-cloning site polylinker into the EcoRI site of pRK290 (FIG. 8). The kanamycin resistance gene was removed by BamHI digestion, and the plasmid was religated to give pJB151. The polylinker remained at the former EcoRI site, providing a number of convenient restriction endonuclease sites for the insertion of promoter::nifA fusions. Any of the fusions described below can be inserted into pJB151, at any of several sites.

Construction of Promoter::nifA Gene Fusions

Kan Promoter::R. meliloti nifA pVW60 contains the Tn5 kanamycin resistance structural gene and its constitutive promoter. It was constructed by ligating the HindIII-SalI fragment from pMS1000 (Filser et al., 1983, Mol. Gen. Genet. 191:485) into HindIII and SalI digested pBR327. The HindIII-SalI fragment of pVW60 was excised and cloned into the HindIII-SalI site of pACYC184 (FIG. 4) yielding pJB98.

Figure 9:
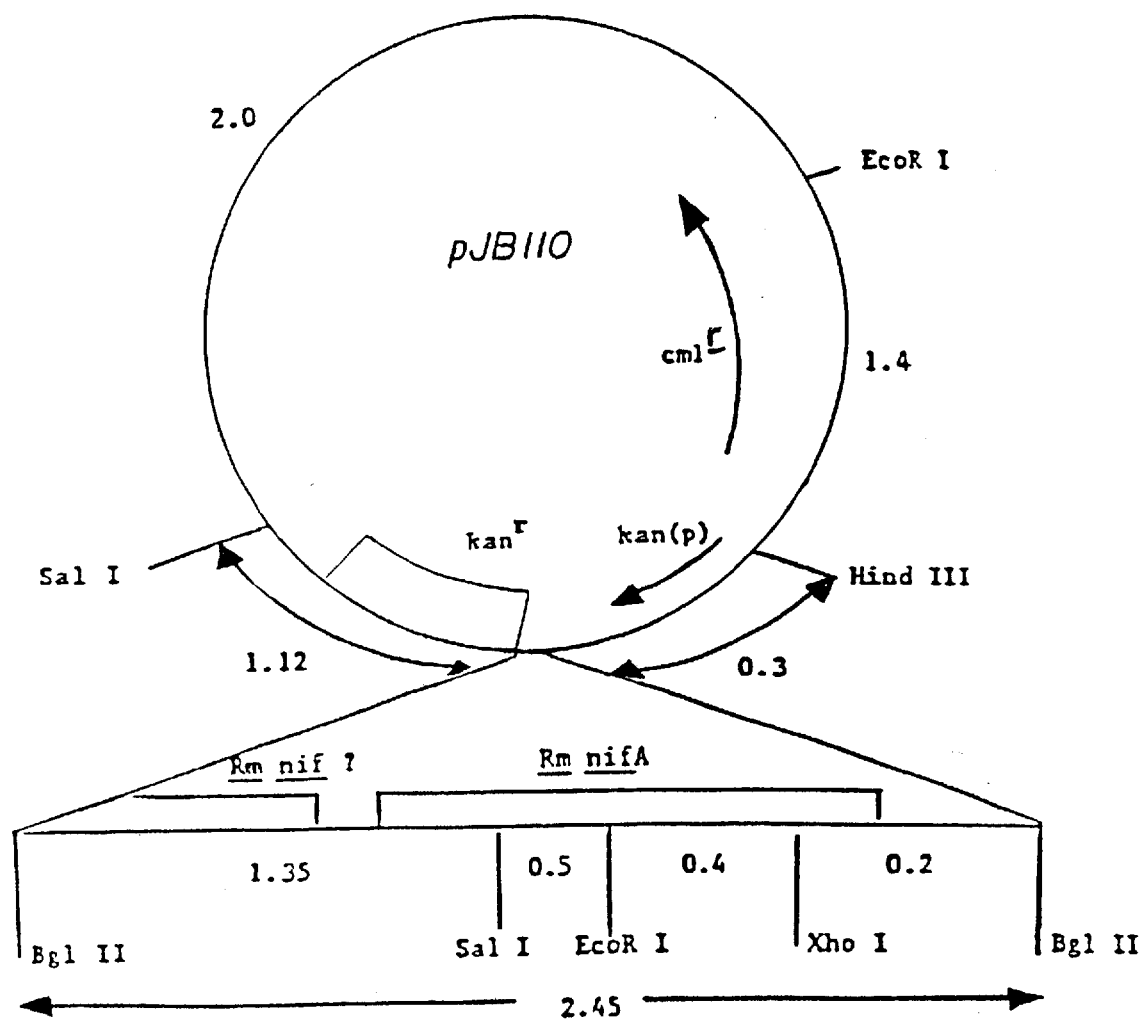
FIG. 9 is a diagrammatic representation of pJB110, a vector used in the construction of the vector of FIG. 10.

The HgiAI fragment carrying the R. meliloti nifA gene was isolated from pRmB3.8H (FIG. 1). BglII linkers were added so that the fragment could be cloned into pJB98 at the BglII site, which lies between the structural gene for kanamycin resistance and its promoter. This step yielded pJB110 (FIG. 9) in which the R. meliloti nifA gene is constitutively expressed from the Tn5 kanamycin resistance gene promoter.

Figure 10:
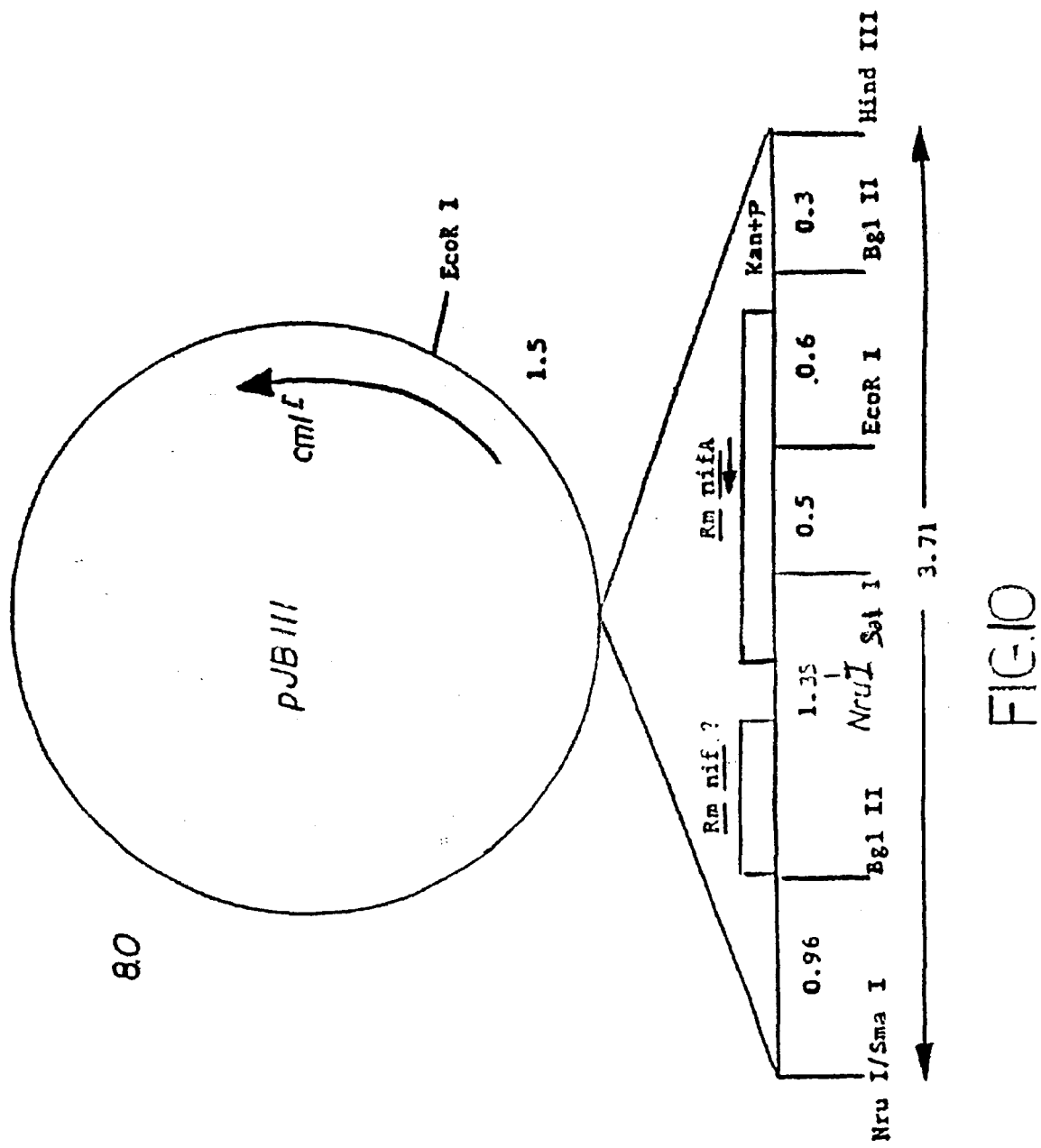
FIG. 10 is a diagrammatic representation of the vector pJB111, containing the R. meliloti nifA gene fused to the kanamycin resistance gene promoter.

In order to insert the desired construction into the broad host range vector pSUP104, pJB110 was digested with HindIII and SmaI and the HindIII-SmaI fragment containing the Tn5 kanamycin resistance gene promoter::R. meliloti nifA gene fusion was isolated and cloned into the HindIII-NruI site of pSUP104 to yield plasmid pJB111 (FIG. 10).

The insert fragment carried on pJB110 and pJB111 also contains a portion of the R. meliloti nifB gene, including its promoter. The presence of the nifB promoter could be detrimental to increasing nitrogen fixation since, as a nitrogen-regulated promoter, it contains a binding site for nifA protein, and would serve to titrate nifA protein away from the promoters to which it is desired that nifA protein bind. We therefore subcloned the nifA gene from pJB110, on a restriction fragment not containing the nifB promoter, as follows.

An NruI site was discovered to be located 24 bp downstream from the end of the nifA gene, in addition to three other NruI sites within the plasmid. pJB110 was digested partially with NruI; full-length linear DNA was isolated, and a BglII linker was ligated in. This resulted in four derivatives that had new BglII sites. Plasmid pJB131 was the derivative which contained a BglII site in the desired location. This permitted the nifA gene to be isolated on a 1.7 kb BglII fragment free of the nifB promoter. The above described procedure can also be performed on pJB111, to yield the same BglII fragment.

Referring to FIG. 11 Panel A, an additional change was made to increase expression of the R. meliloti nifA gene, involving the Shine-Dalgarno (SD) sequence. The natural SD sequence preceding the nifA gene is a relatively weak ribosome binding site based on a comparison with other known SD sequences. We chose to replace the original SD sequence of the nifA gene in pJB160 (carrying a R. meliloti fixA promoter::R. meliloti nifA gene fusion; see above, and FIG. 6) with a synthetic DNA sequence that more closely resembles the E. coli 16S RNA ribosome binding site. pJB124 was cleaved with BglII and ligated with the above described BglII nifA fragment of pJB98 to form pJB140; the BglII site, downstream of nifA gene was changed to PstI, using linkers, to form pJB152; and an EcoRI site upstream of the fixA promoter in pJB152 was changed to HindIII, to give pJB160. This DNA was partially digested with FspI, which cuts just after the first ATG of the nifA gene. A 39 bp fragment was synthesized having a BglII sticky end on the 5' terminus. The sequence of the synthetic DNA recreates the original ATG and the FspI restriction site, as well as changing the SD sequence. Ligation of FspI digested plasmid with the synthetic fragment was followed by BglII digestion (to cut the gene just upstream of the natural SD) and religation to insert the new SD sequence. A clone was selected which had the linker inserted in the correct location. This plasmid is pJB180. Another plasmid derived from pJB180 which contains a cat promoter in place of the fixA promoter is pJB182.

B. japonicum nifH::R. meliloti nifA

Figure 12:
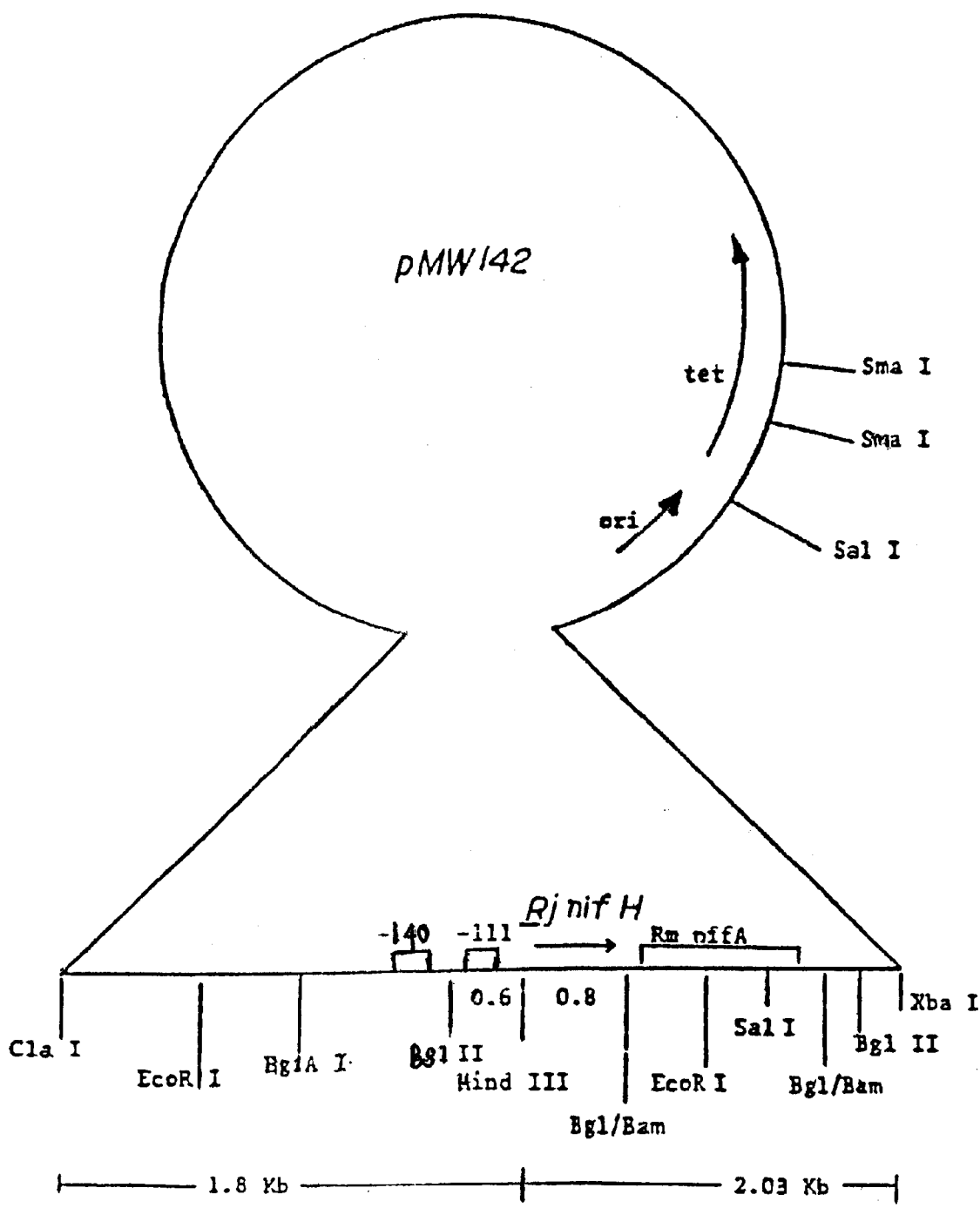
FIG. 12 is a diagrammatic representation of the vector pMW142 containing the R. japonicum nifH promoter fused to the R. meliloti nifA gene.

The 1.7 kb BglII fragment from pJB131 containing the R. meliloti nifA gene with its natural SD sequence was cloned into the BamHI site of pMW126 to give pMW128, in which the nifA gene is under the control of the B. japonicum nifH promoter. To transfer the fusion into a pRK290-based vector, the SalI fragment was removed from pMW128, and the termini were converted to ClaI sites with linkers, followed by ClaI+XbaI digestion. The 3.4 kb ClaI-XbaI fragment, containing the entire B. japonicum nifH promoter and the two upstream binding sequences in addition to the R. meliloti nifA gene, was cloned into ClaI+XbaI digested pJB151 (FIG. 8) to yield plasmid pMW142 (FIG. 12).

Cat promoter::R. meliloti nifA (original SD)

The nifA gene was excised from pJB131 on a 1.7 kb BglII fragment and cloned into the BglII site of pJB120, adjacent to the cat promoter, to give pJB135 (FIG. 13). To transfer this to pJB151, a PvuII fragment containing both the cat promoter and the nifA gene was excised from pJB135. The ends were converted to HindIII by the addition of synthetic linkers and the fragment was cloned into the HindIII site of pJB151, resulting in pJB154 (FIG. 13).

B. japonicum nifH::new SD/R. meliloti nifA

Figure 14:
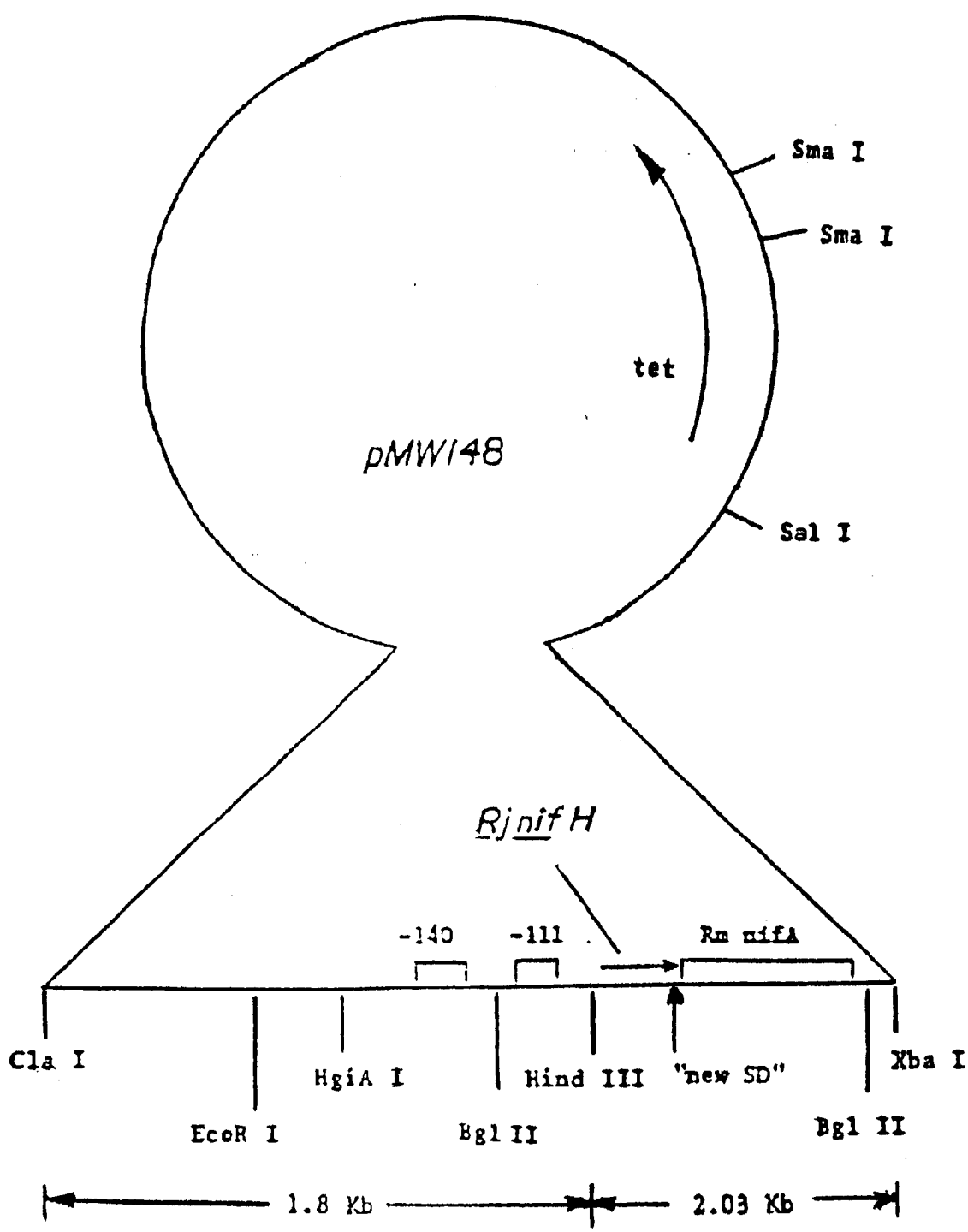
FIG. 14 is a diagrammatic representation of the vector pMW148, containing the R. japonicum nifH promoter fused to the R. meliloti nifA gene preceded by a synthetic Shine-Dalgarno sequence.

The R. meliloti nifA gene preceded by the synthetic SD sequence was removed from pJB182 by the following method. The plasmid was cleaved with PstI and the site was converted to a BglII site with a synthetic linker. Subsequent digestion with BglII released a 1.7 kb fragment containing the nifA gene. This fragment was ligated with BamHI digested pMW126 to give pMW145 in which the R. meliloti nifA gene was under the control of the B. japonicum nifH promoter in a pSUP104 vector backb one. The HindIII-XbaI fragment of pMW145 which spans the nifA gene including the synthetic SD sequence, was cloned into HindIII+XbaI digested pMW142 (FIG. 12), thereby replacing the authentic nifA gene fusion in a pRK290 derived backbone. The final plasmid is designated pMW148 (FIG. 14).

Cat::new SD/R. meliloti nifA

Figure 15:
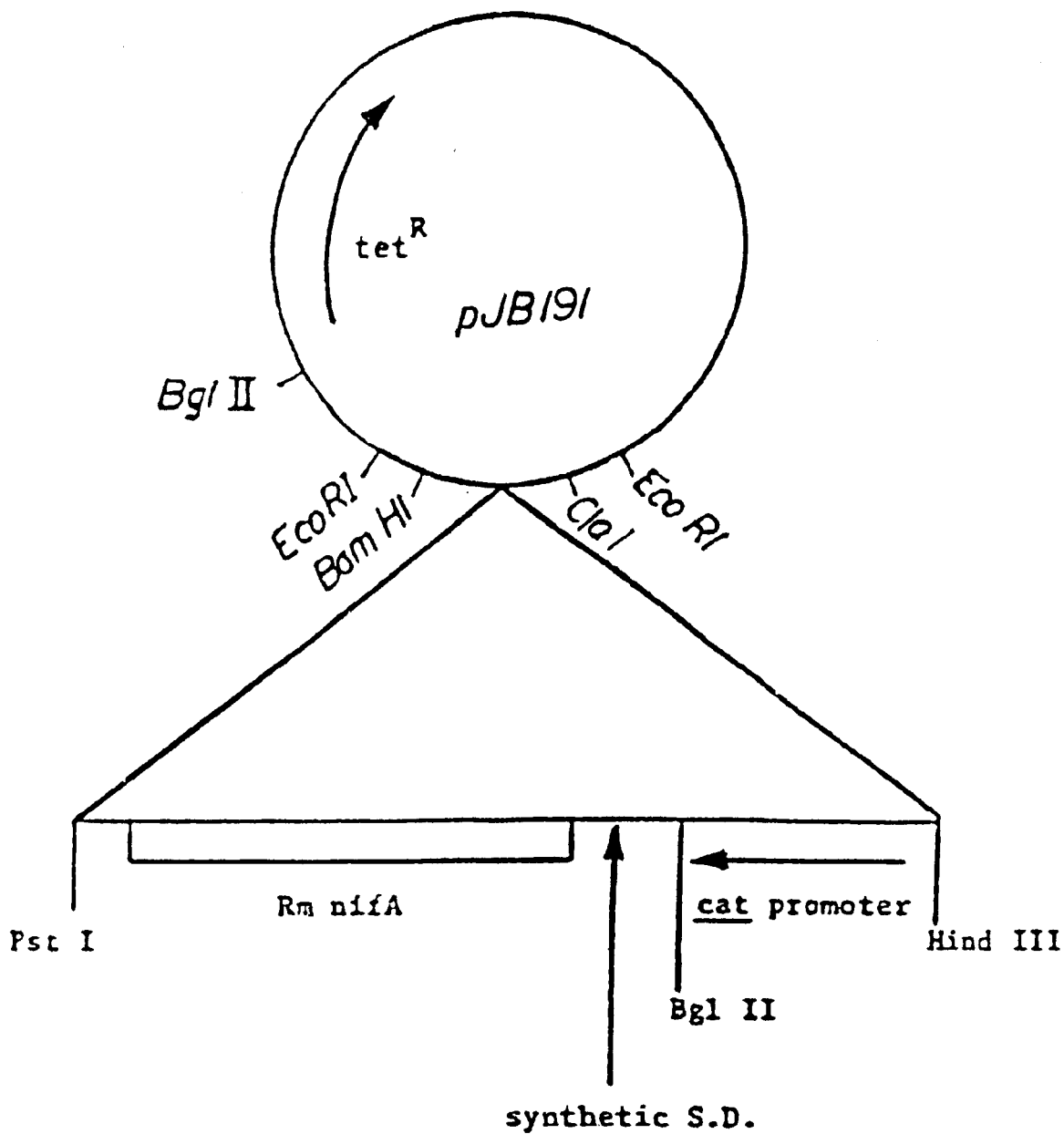
FIG. 15 is a diagrammatic representation of the vector pJB191, containing the R. meliloti nifA gene preceded by a synthetic Shine-Dalgarno sequence and fused to the cat promoter.
Figure 16:
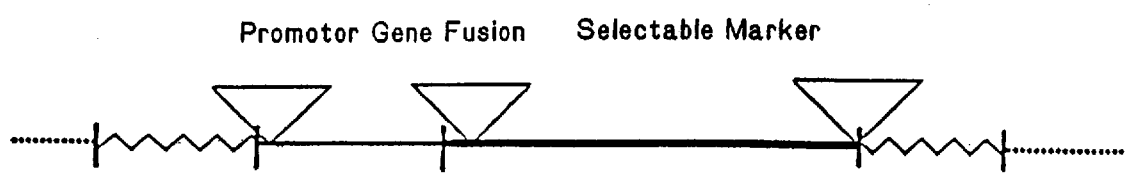
FIG. 16 is a diagrammatic representation of an insertion vector.

The R. meliloti nifA gene was cloned under control of the cat promoter by removing the BglII-PstI fragment from pJB180 and ligating it with BglII+PstI digested pJB167 (derived by digesting pTR1300, 1986, J. Virol. 60:1075, with BglII, and ligating the fragment containing the lac genes into BglII-digested pJB120, to give pRK1301; the NcoI site following the lacZ gene was converted to PstI to give pJB163, and the XmnI site was converted to HindIII to give pJB167), a cat::lacZ fusion vector, resulting in the replacement of the lacZ gene. The cat promoter::nifA fusion was then removed from the new construct (pJB182) by digestion with HindIII and PstI and cloned into HindIII+PstI digested pJB151 (FIG. 8). This resulted in plasmid pJB191 (FIG. 15).

Cat::B. japonicum nifA

The cat promoter::B. japonicum nifA fusion construct (pRAR566) was described above. To reclone the fusion into pJB151, the PvuII fragment was excised from pRAR566, the ends were converted to HindIII with synthetic linkers and then ligated into the HindIII site of pJB151 (FIG. 8) to generate pRAR576.

Microorganism Hosts

Any Rhizobium or Bradyrhizobium strain is a suitable host, particularly one that is an effective nodulator. Suitable hosts for transfer of recombinant plasmids include the following: R. meliloti strain RCR2011, strain SU47 and strain 41; B. japonicum strain USDA 136; B. japonicum strains USDA 110 and USDA 123; R. fredii strain USDA 205. These and many other known strains are publicly available from the ATCC or from the Rothamsted Collection of Rhizobium (Rothamsted Experimental Station, Harpenden, Hertfordshire, U.K.). In addition, the IBP World Catalogue of Rhizobium Collections (Allen et al., 1973, International Biological Programme, London) provides a listing of inocula available worldwide.

Certain indigenous strains can be isolated from the field as representing dominant species (Jenkins et al., 1985, Soil Science of America J., 49:326; Phillips et al., 1985, p.203). Many other strains are known which are highly competitive and effective nodulators. These strains are, of course, considered to be included in the invention.

Transfer of Plasmids to Rhizobium by Triparental Cross

Recombinant plasmids are transferred to the desired host Rhizobium species by a triparental cross, utilizing the helper plasmid pRK2013 (Figurski and Helinski 1979, Proc. Nat. Acad. Sci. U.S.A. 76:1648) as follows. The plasmids were first transformed into E. coli strain, e.g., MM294 (ATCC #33625; 1968, Nature, 217:1110) by conventional methods. Cultures of the recipient Rhizobium strain, E. coli/pRK2013 (which supplies tra and mob functions in trans), and the E. coli strain transformed with a nif recombinant plasmid are mixed on LA agar plates and incubated overnight at 30° C. for conjugation. Such crosses result in the transfer of the plasmids into the host Rhizobium strain by conjugation. Transconjugants are selected on medium containing the appropriate selection for the recipient Rhizobium strain and the nif recombinant plasmids. Plasmid pRK2013 is not stable in Rhizobium and hence is not recoverable from the cross.

Integration

In order to ensure that the constructs described above will be maintained in host cells, and to avoid variation in plasmid retention from strain to strain, it is beneficial to integrate the promoter::gene fusions into the chromosome of an appropriate host rather than maintain them as extrachromosomal elements. Such integration helps to overcome variations observed in plasmid retention, which make it difficult to correlate nifA levels in the bacteroid with changes in plant biomass. Therefore, vectors for the integration or insertion of nif gene fusions into the bacterial chromosome were constructed.

One type of insertion vector is able to cause insertion of DNA at a specific location in the bacterial genome. Such site-specific insertion vectors not only allow transfer of the cloned genes to the bacterial host, but preferably also have some system of instability. One such system is termed marker rescue, where integration of the desired sequences into the chromosome gives rise to a selectable phenotype. An example is the vector pRK290, or a derivative thereof. This vector becomes unstable in the presence of an incompatible plasmid. Thus, marker rescue can be used to select for cells with integrated vector sequences after introducing an incompatible plasmid into the cell containing the vector (see below).

A genomic region of the host chromosome is identified for integration of the desired DNA. Preferably this region is symbiotically silent, i.e., nodule infectiveness, as well as effectiveness, is maintained. The insertion of a desired DNA sequence at a chosen site in the host chromosome should also have little or no effect on the growth of the bacteria, and all metabolic and catabolic activities, other than those specifically altered by the insertion, remain at about wild-type levels.

The vectors preferably contain a "cassette" which comprises all of the elements destined for integration. In this way, the components of the cassette can be replaced with other analogous components using the same vector backbone. The cassette preferably includes (1) a transcriptional promoter fused to a desired gene or genes, particularly genes involved in the enhancement of nitrogen fixation, for example the nifA gene, to form an operon, (2) a selectable marker gene for the selection of integrants carrying the cassette, (3) transcriptional and translational termination signals flanking or, in some cases, intervening between the above described genes to prevent transcriptional read-through from promoters in the adjacent chromosomal DNA and to prevent overexpression of chromosomal genes located downstream of the inserted cassette, and (4) approximately 3–6 kb of flanking DNA sequences homologous to a silent region of the host genome. These flanking sequences, referred to herein as the "homology region", facilitate the integration of foreign DNA by reciprocal recombination.

Components of the integration vector are described in detail below.

Components of an Integration Vector

Cassette-Carrying Vector pIC-20H was chosen as the initial cloning vector for construction of the cassette because it is a relatively small plasmid which contains an extensive polylinker. pIC-20H is a pUC derived plasmid with a polylinker containing approximately 16 unique restriction sites located within the β-galactosidase gene (FIG. 18) (Marsh et al., 1984, Gene 32, 482). Any other vector is equally suitable in this invention.

The "homology region"

R. meliloti integration vector

In order to identify a symbiotically silent region of the R. meliloti chromosome, we selected a mutant having a defect in a known pathway that did not appear to suffer in growth or symbiotic associations with plants. The chosen pathway, which is not crucial for cell growth, leads to the degradation of myo-inositol to utilizable carbon sources (Anderson et al., 1971, J. Biol. Chem. 246:5662.). The first step in this pathway is catalyzed by an NAD+-dependent dehydrogenase (inositol dehydrogenase) which is inducible only by myo-inositol. This pathway is not induced by other polyols and should not be active under normal growth conditions, since inositol is not naturally present in soils. The selected mutant in the inositol utilization pathway, designated Rm $Ino^1$, was generated by Tn5 insertion mutagenesis of R. meliloti strain 1021 followed by selection for the inability to utilize the sugar myo-inositol as its sole carbon source.

A number of other polyol dehydrogenases are known that are induced by oneor more specific polyols (Primrose and Ronson, 1980, J. Bact. 141:1109) and that are not required under normal growing conditions or when in symbiotic association with a plant. These and other symbiotically silent regions of the chromosome may also serve as suitable sites for the integration of heterologous DNA, and may either encode or regulate an enzyme of the chosen pathway or affect transport of the polyol.

The enzyme inositol dehydrogenase (IDH), which is responsible for the conversion of inositol to a utilizable carbon source, was assayed in Rm $Ino^-$ and compared with the activity in R. meliloti 1021, the wild-type parent. No detectable activity was expressed in the mutant strain. However, in plant biomass assays no detectable differences were observed between the mutant strain and the R. meliloti 1021 parent. A DNA region involved in the utilization of myo-inositol (the site of Tn5 insertion) was thus selected as an appropriate site for integration of nif fusions into the Rhizobium genome. This silent genetic region is universally applicable for integrating DNA sequences and should not be limited to DNA sequences of the invention described here.

In order to construct a vector for integration of a DNA segment into a specific genomic location, it is necessary to isolate and clone the homology region. The nifA fusions can then be inserted within this sequence, leaving flanking sequences on either side. Homologous recombination with genomic sequences on either side of the cassette results in its insertion into the genome.

To isolate the selected homology region, a cosmid bank was prepared from R. meliloti DNA by cloning fragments of a partial Sau3A digestion into the BamHI site of pRAR512. PRAR512 was derived from pLAFR1, (Friedman et al., 1982, Gene 18, 289) by inserting a BamHI linker at the EcoRI site which recreates an EcoRI site on either side of the BamHI site. Fragments inserted at the BamHI site can be excised by EcoRI digestion. The cosmid bank was crossed into the Rm $Ino^1$ strain and individual clones tested for complementation of the $Ino^-$ phenotype on media containing myo-inositol as the sole carbon source. Only those Rm $Ino^1$ mutants carrying the corresponding complementing DNA sequences were able to grow.

Four complementing cosmids were isolated and mapped to localize the Tn5 insert using BamHI and EcoRI restriction endonucleases. The overlap between the four cosmids determined the approximate location of the Tn5 element within the cloned region. Southern blots were performed using the region of Rm $Ino^1$ DNA containing the Tn5 insert as a probe to confirm the presence and to determine the location in each cosmid of sequences that complement the $Ino^1$ mutant host. (This probe was prepared from the EcoRI insert of pMW161, constructed by cloning EcoRI fragments of R. meliloti 1021 $Ino^1$ mutant DNA into pBR327 and selecting for kanamycin resistance in E. coli (Tn5 contains no EcoRI sites and carries the gene for kanamycin resistance)). The location of Tn5 in the $Ino^1$ mutant was determined by comparing probe hybridization to EcoRI fragments of the cosmid clones with hybridization to the EcoRI fragments of pMW161. Tn5 was found to be inserted within a 6.2 kb EcoRI fragment containing genetic sequences involved in utilization of myo-inositol. This was confirmed by transforming a vector carrying this fragment into the Rm $Ino^1$ strain and assaying for its ability to complement the $Ino^1$ phenotype. This fragment is an example of a suitable silent region for use in an insertion vector.

B. japonicum insertion vector

A silent region of the B. japonicum chromosome was discovered within the nif gene cluster. A plasmid carrying the nif cluster, and used as an insertion vector, was obtained from the Boyce Thompson Institute for Plant Research. This plasmid, pREV1000 (Legocki et al., 1984, PNAS, 81, 5806), can generally be used for integration of DNA into the Bradyrhizobium chromosome by homologous recombination between sequences on the vector and sequences in the chromosome. A 3.4 kb region of B. japonicum DNA carried on pREV1000 is interrupted by a unique HindIII site for the convenient insertion of nifA expression cassettes. Insertion of DNA within this region of the B. japonicum chromosome does not appear to affect its growth or nitrogen fixing capabilities.

Promoter::nifA fusions

Fusions of nif promoters to the nifA genes were constructed as described above. These constructs were modified to contain a universal mRNA leader sequence preceding the ATG codon of the nifA gene in order to avoid variations in nifA expression resulting from variations in the 5' end of the mRNA. By attaching a universal leader sequence to the nifA qene, the transcripts synthesized are identical, independent of the promoter used. The only variable in the fusion, therefore, is the promoter, thus permitting accurate quantitation of promoter strength. To achieve uniformity, it was necessary to make all of the fusions directly between the −1 position of each promoter and the +1 position within the universal leader sequence. An example of such a construction follows.

Figure 17:
FIG. 17 is the nucleotide sequence of a synthetic linker containing a majority of the R. meliloti nifH leader sequence.

The R. meliloti nifH leader sequence was chosen because the levels of protein translation from the nifH transcript are high in plant nodules. A synthetic linker (FIG. 17) was constructed which contains the sequence of the nifH leader, and extends from a BglII sticky 5' end to a Fspl 3' end. This synthetic linker was used to replace the nifA leader region in pJB182 according to the following strategy. pJB182 was digested with Fspl (FIG. 11) and ligated with the synthetic nifH leader; the plasmid was then digested with BglII to regenerate the BglII end of the synthetic linker and to remove the nifA leader within the plasmid. The BglII ends of the linker and the plasmid were then ligated to create pJB200. The resulting nifH leader::nifA gene fusion is preceded by a unique BglII site for convenient insertion of any promoter fragment that has BglII or BamHI ends.

Following insertion of a promoter fragment, the promoter sequence up to the +1 position of the mRNA is then precisely fused to the +1 site within the nifH leader, using the BssH2 site within the nifH leader and a second site within the promoter fragment. The plasmid is digested with BssH2 and the promoter-leader junction fragment is replaced with a synthetic oligonucleotide that recreates this junction by aligning the +1 position of the promoter with the +1 position within the nifH leader.

The B. japonicum nifD promoter was engineered to precede the nifH leader sequence in pJB200 by the following series of steps. pMW121 (carrying the nifD promoter sequence) was partially digested with SphI in order to cleave only at the site just upstream of the promoter sequence. The site was converted to a KpnI site with synthetic linkers and the plasmid was then redigested with BglII to cleave just downstream of the nifD promoter. The BglII-KpnI promoter fragment of pMW121 was cloned in place of the cat promoter, which precedes the R. meliloti nifA gene, in pJB200. pJB200 was treated by partial digestion with HindIII to cut at the site just upstream of the cat promoter. This site was rendered blunt and converted to a KpnI site with a KpnI linker; the plasmid was then digested with BglII to remove the cat promoter and ligated to the BglII-Kpnl nifD promoter fragment. The resulting plasmid is pMW153. pMW153 is then digested with SphI and BssH2. This fragment is replaced with a synthetic oligonucleotide to create a precise promoter-leader fusion.

The engineering of the B. japonicum nifH promoter::R. meliloti nifA gene fusion was performed in a similar manner, by removing the nifH promoter from pMW126 as follows. pMW126 was digested with EcoRI, the site was rendered blunt and converted to a KpnI site with a linker; the plasmid was then digested with KpnI and BamHI and the fragment was cloned into BglII and KpnI digested pJB200. (The KpnI site was created by partially digesting pJB200 with HindIII and inserting a KpnI linker.) The resulting plasmid is pMW154. To create a proper fusion between the +1 position of the promoter and the nifH leader, an oligonucleotide was synthesized having BssH2 sites on either end. This fragment was cloned into pMW154 that had been digested with BssH2 at two locations, within the promoter and also within the leader sequence. The resulting plasmid is pMW190.

For convenience, we have prepared all promoter::nifA fusions with flanking KpnI sites because this enzyme does not cut within the R. meliloti nifA gene or any of the promoter fragments used, and is a unique site in the integration vector polylinker sequence.

Selectable Marker

Figure 18:
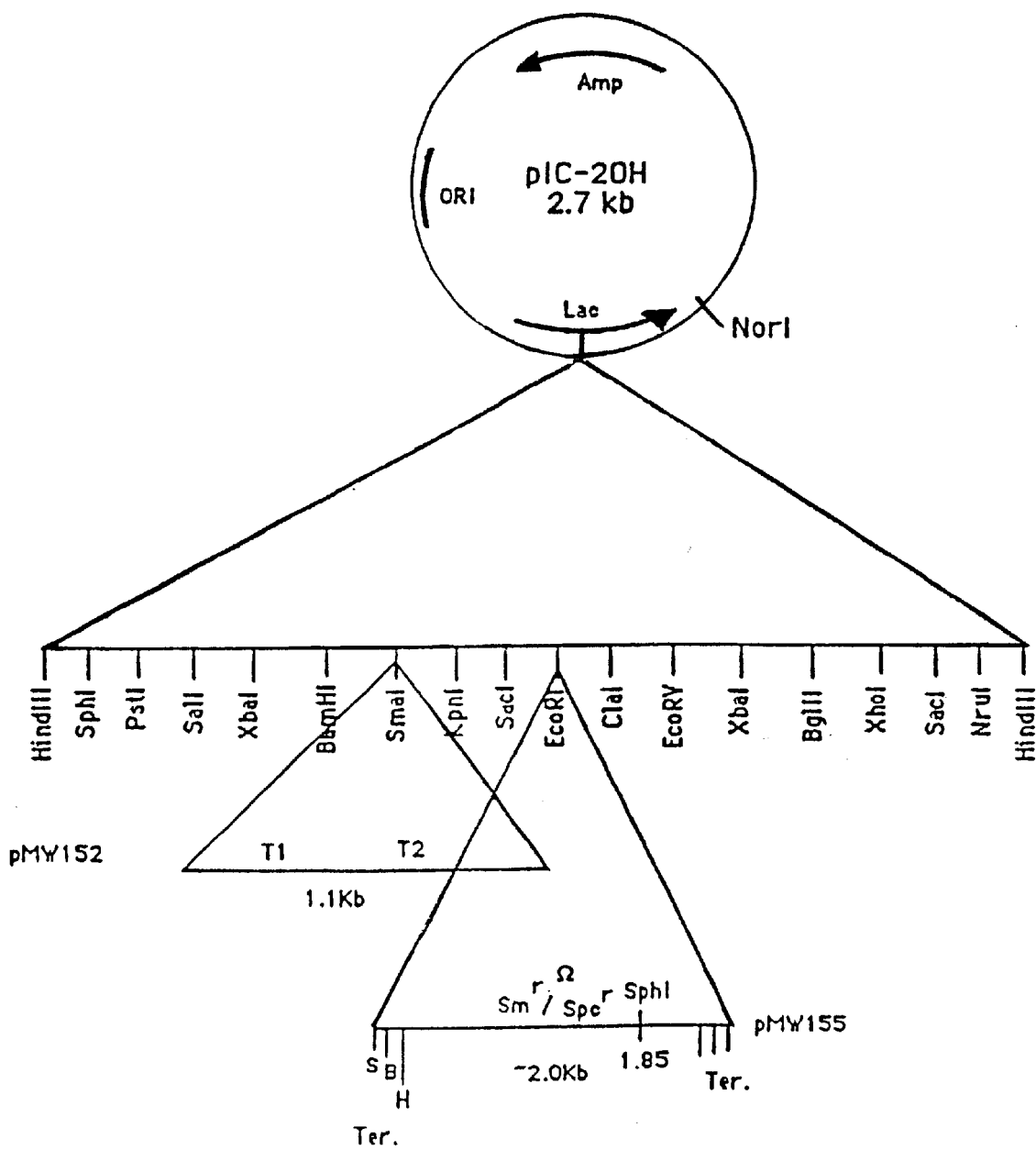
FIG. 18 is a diagrammatic representation of vector pIC-20H and derivatives thereof.
Figure 19:
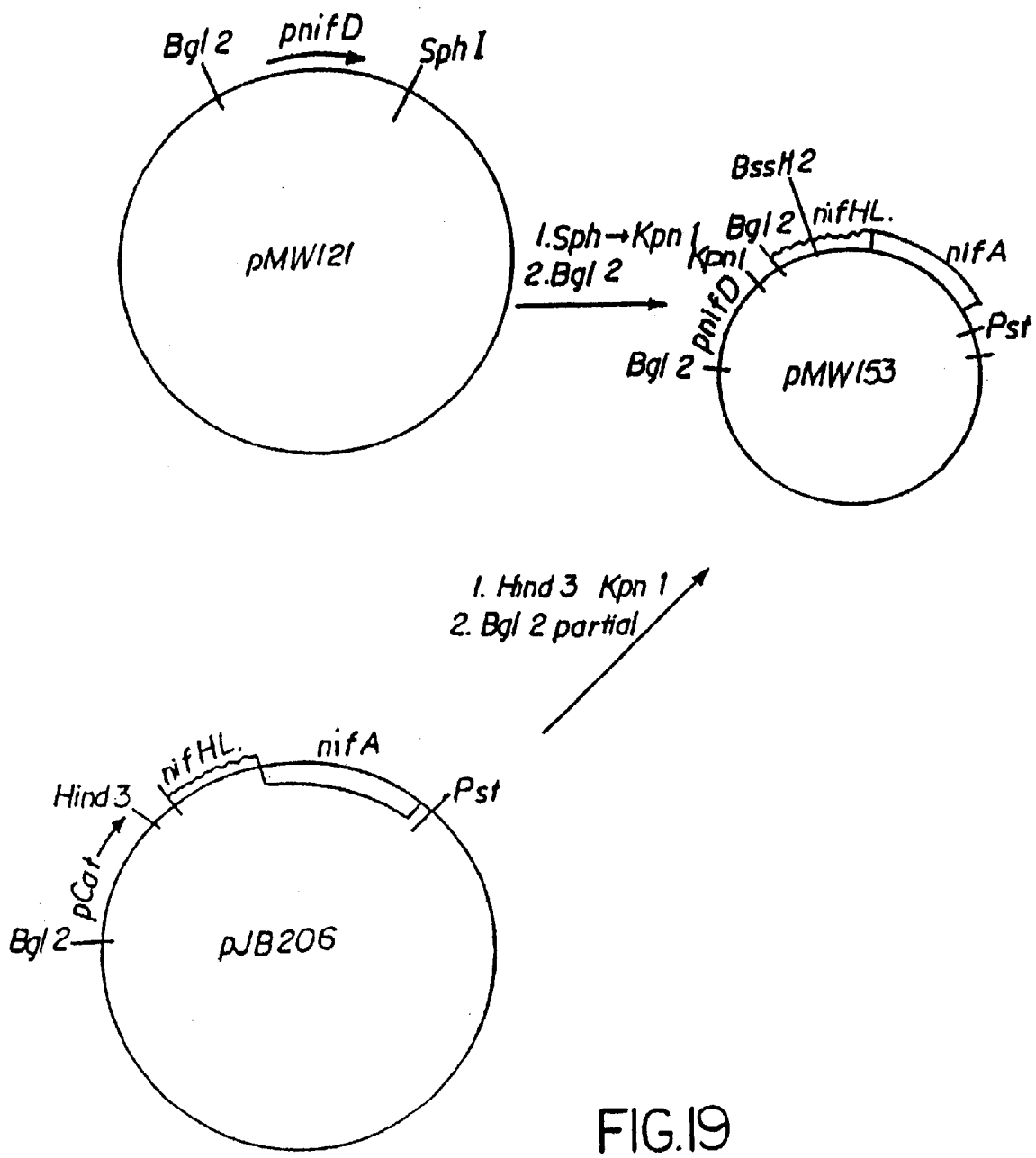
FIG. 19 is a diagrammatic representation of the construction of pMW153, containing the nifD promoter and the nifH synthetic leader fused to the nifA gene.

Any desired selectable marker is suitable in this invention. For example, the selectable marker used below is the spectinomycin/streptomycin antibiotic resistance operon obtained from plasmid pHP45Ω (Prenthi et al, 1984, Gene 29:303). pHP45Ω was constructed by isolating the omega fragment (containing the antibiotic resistance genes) from the IncFII plasmid, R100.1 (Jacob et al., DNA Insertion Elements, Plasmids, and Episomes, eds. Bukhari, Shapiro, and Adhya, Cold Spring Harbor, N.Y., 1978, pp. 607–664), and cloning it into a pBR322 derivative. This set of resistance genes is flanked by short inverted repeats carrying the T4 transcription termination and translation stop signals and a polylinker sequence. The region can be removed from pHP45Ω on a 2.0 kb fragment by digestion with any of a number of restriction enzymes. For construction of the vector of this invention, we isolated the EcoRI restriction fragment and cloned it into EcoRI digested pMW152 (see following section) to create pMW155 (FIG. 18).

Termination Signals

Transcription termination signals are well known in the art and any desired signal is suitable in this invention. For example, a 1.1 kb fragment carrying the T1/T2 transcriptional terminators from the rrnB operon of E. coli (Brosius et al., 1981, J. Mol. Biol. 148:107) was obtained from the vector pEA300 (Molecular Cloning, A laboratory Manual 1982, eds. Maniatis, Fritsch and Sambrook) and cloned into SmaI digested pIC-20H, creating pMW152 (FIG. 18).

The promoter::nifA gene fusions inserted into the KpnI site of the pIC-20H are flanked by transcription termination signals (from the omega fragment and T1/T2) to prevent transcriptional read-through into the adjacent Rhizobium genomic DNA. It is preferable to use different flanking termination signals so as to avoid a recombination event within the cassette.

Process of Integration

Once the dassette is constructed, any suitable vector is used to transfer the cassette into the desired host. A number of restriction sites are available in the polylinker sequence for removal of the cassette from pIC-20H. Integration is induced by standard procedures. The following is an example demonstrating the use of pRK290 (Helinski, U.S. Pat. No. 4,590,163) as the cloning vector.

The cassette, containing the B. japonicum nifA promoter::R. meliloti nifA gene fusion and the omega fragment is removed from the pIC-20H based vector on an XbaI fragment (the EcoRV site in the pIC-20H polylinker was converted to an XbaI site) and cloned into the SpeI site of the pRK290 derivative, pMW184. (pMW184 was derived from a pRK290 based plasmid containing the 6.2 EcoRI inositol fragment by first digesting with HpaI and Bal 31 to remove the Tn5 sequence, then inserting SpeI linkers to create a unique site for cloning of the integration cassette.) This construct, which now contains the cassette flanked by the homology region, and an incompatible plasmid, e.g., pJB251, carrying the gentamycin resistance selectable marker gene, are introduced into the R. meliloti host RCR2011. (pJB251 was derived from pPH1 (Hersh et al., 1984, Plasmid 12:139) by doing a partial HindIII digestion to delete the spectinomycin gene and then selecting for gentamycin$^r$, and screening for spectinomycin$^s$.) Recipients are selected for expression of both spectinomycin and gentamycin resistances. Since the two plasmids are incompatible, these genes will only be expressed simultaneously if the cassette has integrated into the chromosome or if the vectors have recombined with each other. To distinguish between the two cases, the transformants are screened for tetracycline sensitivity, i.e., loss of the pRK290-derived vector, and for the lack of ability to grow on myo-inositol as a carbon source, indicating that the cassette has integrated into the genome. The DNA of the integrants is then analyzed by conventional procedures to confirm that integration has occurred.

The recipient host is subsequently cured of the pJB251 plasmid by allowing the strains to nodulate alfalfa, re-isolating the bacteria and screening for those that were spectinomycin resistant and gentamycin sensitive. These isolates are then tested on alfalfa to determine the effect on plant biomass.

Microorganisms and Legumes

The species of modified nitrogen fixing bacteria employed depends on the plant species to be inoculated. Generally, it is preferred that the same bacterial species which naturally associates with the plant species be employed as the host species for the vector of the invention. For example, where the legume is alfalfa (*Medicago sativa*), the modified host bacterium is preferably R. meliloti; where the legume is soybean (*Glycine max*), the bacterium is preferably R. japonicum; where the legume is the bean *Phaseolus vulgaris*, the bacterium is preferably R. phaseoli; and where the legume is clover, the bacterium is preferably R. trifolii. In addition to Rhizobium species, the invention can be applied to other natural nitrogen-fixing bacterial species, as well as to microorganisms into which nitrogen fixing genes have been inserted via recombinant DNA techniques.

Inoculation of Plants

Inoculation of plant seeds with recombinant Rhizobium can be performed by the following procedure, (See "A Manual for the Study of Root Nodule Bacteria", ed. Vincent, 1970, Blackwell Scientific Publishers, Oxford and Edinborough, pp.113–131 for general procedures.). Raw seeds are sterilized in a 10% solution of Sodium Hypochlorite for 20 minutes followed by extensive rinsing with distilled water. Seeds are then spread into a pot containing sterilized vermiculite and placed in the dark for 4 days to germinate. To prepare the inoculant, YM+ media containing the appropriate antibiotics is seeded with Rhizobium cells and grown for 30 hours. The culture is centrifuged to pellet the cells and resuspended in sterile distilled water to a final concentration of about $1 \times 10^9$ cells/ml. The cells are diluted 125× into sterile mineral salts and used to inoculate the 4-day old germinated seedlings. (The final concentration of Rhizobium in each pot is approximately $1 \times 10^7$ cells/ml). The plants are watered appropriately, including once per week with mineral salts. After 4 weeks the plants are harvested.

Commercial Uses of Rhizobia

Product form

Inoculants of rhizobial cultures are used commercially to increase the yields of legume crops and are available in several forms. In one form, cultures are absorbed on a carrier of peat or clay, then applied to seeds as a very thin coating. If mixed with lime and binder, legume seeds become covered with a relatively thick coating, adding up to 50% to the weight of the seeds.

In the second method, cultures are available in a liquid form or preabsorbed on peat for application during planting. Finally, Rhizobia can be absorbed on large particle size peat for direct application in a seed furrow of a planter box.

Production

Rhizobium cultures are grown in standard aerobic fermentations and are then generally combined with a carrier of fine powdered peat or clay. This is done by mixing a volume of cell suspension into a specially selected grade of peat or clay, and allowing a certain amount of time for absorption during which the cells continue to grow on the carrier. Cell numbers might increase ten-fold in the peat and with proper storage, these cultures can be held up to nine months before use.

Deposits

Plasmids/pJB111 was deposited in the American Type Culture Collection, Rockville, Md. on Nov. 21, 1984. The above deposit has been given ATCC Accession No. 39931.

Applicants' assignee, BioTechnica International, Inc., acknowledges its responsibility to replace this culture should it die before the end of the term of a patent issued hereon, 5 years after the last request for a culture, or 30 years, whichever is the longer, and its responsibility to notify the depository of the issuance of such a patent, at which time the deposit will be irrevocably made available to the public. Until that time the deposit will be made available to the Commissioner of Patents under the terms of 37 CFR Section 1.14 and 35 USC Section 112.

Other embodiments are within the following claims.

What is claimed is:

1. A method for making a recombinant *Rhizobium meliloti* microbe having a recombinant gene construct that increases capacity of *Rhizobium meliloti* to fix nitrogen, and increases biomass of a plant inoculated with the recombinant *Rhizobium meliloti*, the method comprising:

making a first plasmid vector having an R. meliloti nifA gene;

making a second plasmid vector having a gene encoding sequence for a gene promoter selected from the group consisting of B. japonicum nifH activatable gene promoter and B. japonicum nifD activatable gene promoter;

making a broad host range plasmid vector having a selectable marker gene for transferring the R. meliloti nifA gene and gene promoter to a microbe;

fusing the R. meliloti nifA gene and the gene sequence encoding for the gene promoter to make an R. meliloti nifA gene::promoter gene construct using the broad host range plasmid vector having a selectable marker gene to position the gene construct on the broad host range plasmid vector;

transforming the broad host range plasmid vector into an effective host microbe to make a transformed effective host microbe;

conjugating the transformed effective host microbe with the R. meliloti microbe;

selecting the R. meliloti transformed by the nifA::promoter gene construct by use of a phenotype expressed by the selectable marker gene; and inoculating a plant with the selected R. meliloti, thereby increasing the biomass of the plant once the plant matures.

2. The method of claim 1 wherein the first plasmid vector is selected from the group consisting of plasmid pRMB3.8H, plasmid pJB131, plasmid pJB182 and plasmid pJB203.

3. The method of claim 1 wherein the second vector is selected from the group consisting of plasmid pMW126, plasmid pMW115, plasmid pMW116, plasmid pBJ33, plasmid pMW122, plasmid pRJ676Δ1, plasmid pMW113, plasmid pMW114, and plasmid pMW117.

4. The method of claim 1 wherein the broad host range vector is plasmid pJB151.

5. An *R. meliloti* recombinant microbe produced by the method of claim 1 characterized by a phenotype expressed by the selectable marker gene and by the gene construct that increases the *R. meliloti* microbe's capacity to fix nitrogen and increases the *R. meliloti* microbe's capacity to increase biomass of a plant when in a symbiotic association with the plant.

6. An *R. meliloti* microbe transformed with a plasmid, the plasmid having a selectable marker gene and a gene construct comprising a gene for an *R. meliloti* nifA gene and a gene promoter selected from the group consisting of a *B. japonicum* nifH activatable gene promoter and a *B. japonicum* nifD activatable gene promoter, the *R. meliloti* microbe having a phenotype expressed by the selectable marker gene and further having an increased capacity to fix nitrogen and a capacity to increase biomass of a plant inoculated with the *R. meliloti*.

7. The method of claim 1 wherein a domain A of the *R. meliloti* nifA gene includes a synthetic SD sequence replacing a natural SD sequence.

8. A method for making a recombinant *Rhizobium meliloti* microbe having a recombinant gene construct integrated into the *R. meliloti* microbe's DNA in order to permanently increase the *R. meliloti* microbe's capacity to fix nitrogen, the method comprising:

integrating into a symbiotically silent region of *Rhizobium meliloti* DNA encoding for inositol dehydrogenase (IDH), a cassette comprising:
a transcriptional promoter gene selected from the group consisting of a *B. japonicum* nifH activatable gene promoter, and a *B. japonicum* nifD activatable gene promoter, and fused to an *R meliloti* nifA gene, to form a construct;
a selectable marker gene for the selection of integrants carrying at least one cassette;
effective transcriptional and translational termination signals; and
approximately 3–6 kb of flanking DNA sequences that are homologous to the symbiotically silent region of *Rhizobium meliloti* DNA encoding for IDH.

9. A recombinant DNA plasmid having a cassette encoding for genes comprising:
a transcriptional promoter gene selected from the group consisting of *B. japonicum* nifH and *B. japonicum* nifD fused to an *R. meliloti* nifA gene to form a construct;
a selectable marker gene for the selection of integrants carrying the cassette;
transcriptional and translational termination signals to prevent transcriptional read through; and
approximately 3–6 kb of flanking DNA sequences that are homologous to a symbiotically silent region of *Rhizobium meliloti* DNA encoding for inositol dehydrogenase (IDH).

10. A recombinant *Rhizobium meliloti* microbe permanently transformed with an insertion plasmid inserted at a symbiotically silent region of *R. meliloti* DNA encoding for inositol dehydrogenase (IDH), the insertion plasmid encoding for a cassette comprising:
a gene promoter selected from the group consisting of *B. japonicum* nifH and *B. japonicum* nifD fused to an *R. meliloti* nifA gene to form a construct;
a selectable marker gene for the selection of integrants carrying the cassettes;
transcriptional and translational termination signals to prevent transcriptional read through; and
approximately 3–6 kb of flanking DNA sequences that are homologous to the symbiotically silent region of Rhizobium meliloti DNA encoding for inositol dehydrogenase (IDH).

11. A method for making a recombinant *Bradyrhizobium japonicum* microbe having a recombinant gene construct that increases the *Bradyrhizobium japonicum* microbe's capacity to fix nitrogen, the method comprising:
making a first plasmid vector having a gene encoding for *B. japonicum* nifA;
making a second plasmid vector that includes an *R. meliloti* fixA gene promoter;
making a broad host range plasmid vector having a selectable marker gene, the plasmid vector for transferring the *B. japonicum* nifA gene sequence and the promoter gene sequence to a microbe;
fusing the *Bradyrhizobium japonicum* nifA gene sequence and the *R. meliloti* fixA gene promoter sequence to make a *B. japonicum* nifA gene::promoter gene construct using the broad host range plasmid vector to position the gene construct on the broad host range plasmid vector;
transforming the broad host range plasmid vector into an effective host microbe to make a transformed effective host microbe;
conjugating the transformed effective host microbe with the *Bradyrhizobium japonicum* microbe to form a transformed host;
selecting the *B. japonicum* transformed by the nifA::promoter gene construct by use of a phenotype expressed by the selectable marker gene; and
inoculating a plant with the selected *B. japonicum* thereby increasing the biomass of the plant once the plant matures.

12. The method of claim 11 wherein the first plasmid is selected from the group consisting of plasmid pRAR566 and pFCC301.

13. The method of claim 11 wherein the second plasmid vector is selected from the group consisting of plasmid pJB124, pWB1083, and pJB117.

14. The method of claim 11 wherein the broad host range vector is plasmid pJB151.

15. A recombinant *B. japonicum* microbe produced by the method of claim 11 characterized by a phenotype expressed by the selectable marker gene and by the recombinant gene construct that increases the *B. japonicum* microbe's capacity to fix nitrogen and increases the *B. japonicum* microbe's capacity to increase biomass of a plant when in symbiotic association with the plant.

16. A *Bradyrhizobium japonicum* microbe transformed with a plasmid, the plasmid having a selectable marker gene and a recombinant gene construct comprising a gene encoding for *Bradyrhizobium japonicum* nifA and a gene encoding for an *R. meliloti* fixA gene promoter, the *Bradyrhizobium japonicum* microbe having a phenotype expressed by the selectable marker gene and further having an increased capacity to fix nitrogen and a capacity to increase biomass of a plant inoculated with the *Bradyrhizobium japonicum*.

17. A method for making a recombinant *Bradyrhizobium japonicum* microbe having a recombinant gene construct integrated into the *Bradyrhizobium japonicum* microbe DNA in order to permanently increase the *Bradyrhizobium japonicum* microbe's capacity to fix nitrogen, the method comprising:

integrating into a Hind III site of a silent region of *Bradyrhizobium japonicum* DNA located within a nif gene cluster of *Bradyrhizobium japonicum*, a cassette comprising:

a *Rhizobium meliloti* fixA promoter gene fused to a *Bradyrhizobium japonicum* nifA gene to form a gene construct;

a selectable marker gene for the selection of integrants carrying at least one cassette;

transcriptional and translational termination signals; and approximately 3–6 kb of flanking DNA sequences that are homologous to the Hind III site of the silent region located within the nif cluster of *Bradyrhizobium japonicum* DNA.

18. A *Bradyrhizobium japonicum* bacterium transformed with an insertion plasmid inserted at a Hind III site within a silent region of a nif gene cluster of *Bradyrhizobium japonicum* DNA, the insertion plasmid encoding for an *R. meliloti* fixA gene promoter fused to a nifA gene to form a gene construct; DNA sequences homologous to the Hind III site within the silent region of the nif gene cluster of *Bradyrhizobium japonicum* DNA flanking either side of the gene construct; a sequence encoding for a selectable marker gene; and effective transcriptional and translational termination signals.

19. A recombinant DNA plasmid having a cassette encoding for genes comprising:

an *R. meliloti* fixA gene promoter fused to a *Bradyrhizobium japonicum* nifA gene to form a gene construct;

a selectable marker gene for the selection of integrants carrying at least one cassette;

transcriptional and translational termination signals to prevent transcriptional read through; and approximately 3–6 kb of flanking DNA sequences that are homologous to a Hind III site of a silent region of *Bradyrhizobium japonicum* DNA located within a nif gene cluster of *Bradyrhizobium japonicum*.

* * * * *

UNITED STATES PATENT AND TRADEMARK OFFICE
CERTIFICATE OF CORRECTION

PATENT NO. : 6,548,289 B1  
DATED : April 15, 2003  
INVENTOR(S) : James I. Beynon et al.

Page 1 of 1

It is certified that error appears in the above-identified patent and that said Letters Patent is hereby corrected as shown below:

Column 1,
Line 62, delete "closer", insert -- clover --.

Column 4,
Line 33, delete "operation,", insert -- operation --

Column 11,
Line 40, delete "backb one.", insert -- backbone --

Column 13,
Line 55, delete "oneor", insert -- one or --

Column 19,
Lines 29 & 30, after "sequence", delete "replacing a natural SD sequence.

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,548,289 B1
DATED          : April 15, 2003
INVENTOR(S)    : James L. Beynon et al.

It is certified that error appears in the above-identified patent and that said Letters Patent is hereby corrected as shown below:

<u>Title page,</u>
Item [63], delete "Continuation of application No. 07/181,430, filed on Apr. 14, 1988, now abandoned." and insert -- Continuation of application No. 07/181,430, filed on Apr. 14, 1988, now abandoned, which is a continuation of 06/910,602, filed Sep. 23, 1986, now abandoned, which is a continuation-in-part of 06/687,384, filed on Dec. 28, 1984, now abondoned. --

Signed and Sealed this

Twentieth Day of January, 2004

JON W. DUDAS
*Acting Director of the United States Patent and Trademark Office*